(12) United States Patent
Bogner et al.

(10) Patent No.: US 10,806,099 B2
(45) Date of Patent: Oct. 20, 2020

(54) SYSTEM AND METHOD FOR PROVIDING CARBON DIOXIDE AND CIRCULATING AIR FOR A VERTICAL GARDENING SYSTEM

(71) Applicant: Vertical Air Solutions LLC, Aptos, CA (US)

(72) Inventors: Matthew Lawrence Bogner, Watsonville, CA (US); James Allen Cunningham, Aptos, CA (US)

(73) Assignee: Vertical Air Solutions LLC, Aptos, CA (US)

( * ) Notice: Subject to any disclaimer, the term of this patent is extended or adjusted under 35 U.S.C. 154(b) by 0 days.

(21) Appl. No.: 16/112,077

(22) Filed: Aug. 24, 2018

(65) Prior Publication Data
US 2019/0059242 A1 Feb. 28, 2019

Related U.S. Application Data

(63) Continuation-in-part of application No. 15/730,659, filed on Oct. 11, 2017.

(60) Provisional application No. 62/549,919, filed on Aug. 24, 2017, provisional application No. 62/712,675, filed on Jul. 31, 2018.

(51) Int. Cl.
| | |
|---|---|
| A01G 9/24 | (2006.01) |
| A01G 9/18 | (2006.01) |
| A61L 9/20 | (2006.01) |
| B01D 46/00 | (2006.01) |
| A01G 7/04 | (2006.01) |
| A01G 9/26 | (2006.01) |
| A01G 7/02 | (2006.01) |

(52) U.S. Cl.
CPC ............ *A01G 9/246* (2013.01); *A01G 7/02* (2013.01); *A01G 7/045* (2013.01); *A01G 9/18* (2013.01); *A01G 9/26* (2013.01); *A61L 9/20* (2013.01); *B01D 46/0038* (2013.01); *A61L 2209/134* (2013.01); *A61L 2209/14* (2013.01); *A61L 2209/16* (2013.01)

(58) Field of Classification Search
CPC . A01G 9/18; A01G 9/246; A01G 9/26; A01G 7/045; F24F 7/045; F24F 2007/001
USPC .................................... 47/17, 19.2, 29.5, 39
See application file for complete search history.

(56) References Cited

U.S. PATENT DOCUMENTS

| | | | |
|---|---|---|---|
| 2,034,995 A * | 3/1936 | Sibley | F24F 7/06 |
| | | | 454/345 |
| 3,307,469 A | 3/1967 | Bohanon | |
| 3,348,922 A * | 10/1967 | Bose | A01G 9/18 |
| | | | 422/208 |
| 3,474,720 A * | 10/1969 | Sartain | A01G 9/246 |
| | | | 454/236 |

(Continued)

FOREIGN PATENT DOCUMENTS

| | | |
|---|---|---|
| JP | 2009-273481 A | 11/2009 |
| JP | 2014-014285 A | 1/2014 |

(Continued)

*Primary Examiner* — David J Parsley
*Assistant Examiner* — Danielle A Clerkley
(74) *Attorney, Agent, or Firm* — Levine Bagade Han LLP

(57) ABSTRACT

Vertical growing uses a plurality of shelves to support plants. The system has an air filtration and ultraviolet (UV) air purification system. The purified and filtered air is mixed with nitrogen, which is directed towards plants. The system can include lights to help grow the plants placed on the shelves. The filters can remove odors from the circulating air.

60 Claims, 26 Drawing Sheets

(56) References Cited

U.S. PATENT DOCUMENTS

| | | | | |
|---|---|---|---|---|
| 3,648,591 | A * | 3/1972 | Winnett | B60H 1/3407 |
| | | | | 454/158 |
| 3,810,327 | A * | 5/1974 | Giansante | A01G 18/60 |
| | | | | 47/1.1 |
| 3,956,852 | A * | 5/1976 | Ceausescu | A01G 9/246 |
| | | | | 47/17 |
| 4,030,518 | A * | 6/1977 | Wilcox | E04B 9/02 |
| | | | | 137/246 |
| 4,292,762 | A | 10/1981 | Fogg et al. | |
| 4,505,066 | A | 3/1985 | Moore | |
| 4,589,476 | A * | 5/1986 | Berner | F24F 12/001 |
| | | | | 165/54 |
| 5,358,444 | A * | 10/1994 | Helm | F24F 7/08 |
| | | | | 454/306 |
| 5,493,808 | A * | 2/1996 | Munday | A01G 9/246 |
| | | | | 47/60 |
| 6,205,704 | B1 | 3/2001 | Schmitz et al. | |
| 6,578,319 | B1 | 6/2003 | Cole et al. | |
| 8,468,741 | B2 * | 6/2013 | Lewis | A01G 31/06 |
| | | | | 47/66.6 |
| 9,161,498 | B1 | 10/2015 | Shelor | |
| 9,241,453 | B1 | 1/2016 | Martin et al. | |
| 9,480,207 | B2 | 11/2016 | Tanase et al. | |
| 2004/0194371 | A1 * | 10/2004 | Kinnis | A01G 9/246 |
| | | | | 47/17 |
| 2004/0251122 | A1 * | 12/2004 | Goswami | A61L 2/02 |
| | | | | 204/157.3 |
| 2008/0086981 | A1 | 4/2008 | Kilkis et al. | |
| 2008/0172935 | A1 | 7/2008 | Feng | |
| 2010/0126063 | A1 * | 5/2010 | Emoto | A01G 7/045 |
| | | | | 47/39 |
| 2010/0275512 | A1 | 11/2010 | Nien | |
| 2011/0192082 | A1 | 8/2011 | Uchiyama | |
| 2011/0302838 | A1 | 12/2011 | Chen et al. | |
| 2012/0311926 | A1 | 12/2012 | Mittelmark | |
| 2013/0000185 | A1 | 1/2013 | Tanase et al. | |
| 2013/0305601 | A1 | 11/2013 | Park | |
| 2014/0260131 | A1 | 9/2014 | Burkhauser | |
| 2015/0007495 | A1 | 1/2015 | Tseng et al. | |
| 2015/0230416 | A1 * | 8/2015 | Lo | A01G 25/02 |
| | | | | 47/79 |
| 2016/0007544 | A1 | 1/2016 | Takashima et al. | |
| 2016/0057944 | A1 | 3/2016 | Smits et al. | |
| 2016/0157447 | A1 * | 6/2016 | Hanzawa | A01G 9/247 |
| | | | | 47/60 |
| 2016/0242372 | A1 | 8/2016 | Wong et al. | |
| 2016/0324089 | A1 | 11/2016 | Miyabe et al. | |
| 2018/0125016 | A1 * | 5/2018 | Dufresne | A01G 9/246 |
| 2018/0213735 | A1 * | 8/2018 | Vail | A01G 31/06 |
| 2019/0059241 | A1 | 2/2019 | Bogner et al. | |

FOREIGN PATENT DOCUMENTS

| | | | | |
|---|---|---|---|---|
| JP | 2016208948 A * | 12/2016 | | A01G 9/246 |
| WO | WO-2017024079 A2 * | 2/2017 | | A01G 7/045 |
| WO | WO 2019/040863 | 2/2019 | | |

* cited by examiner

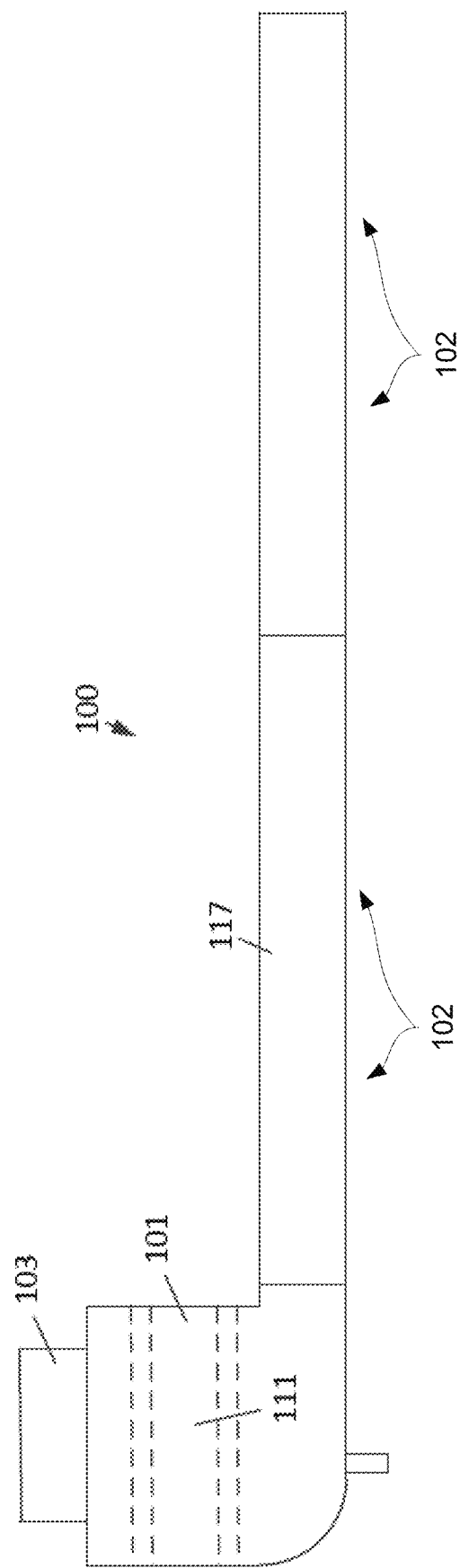

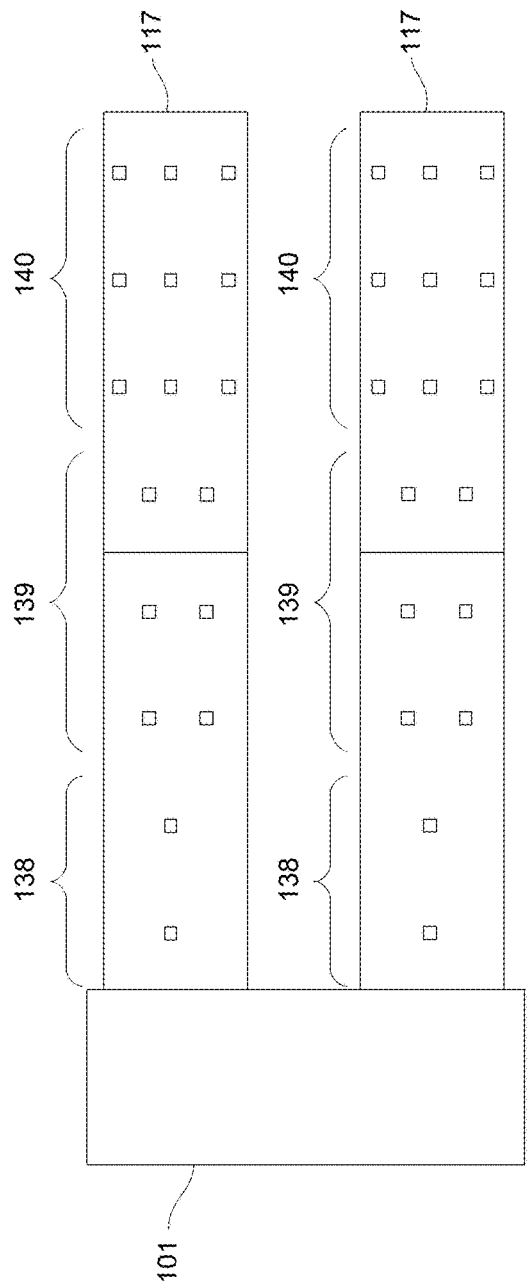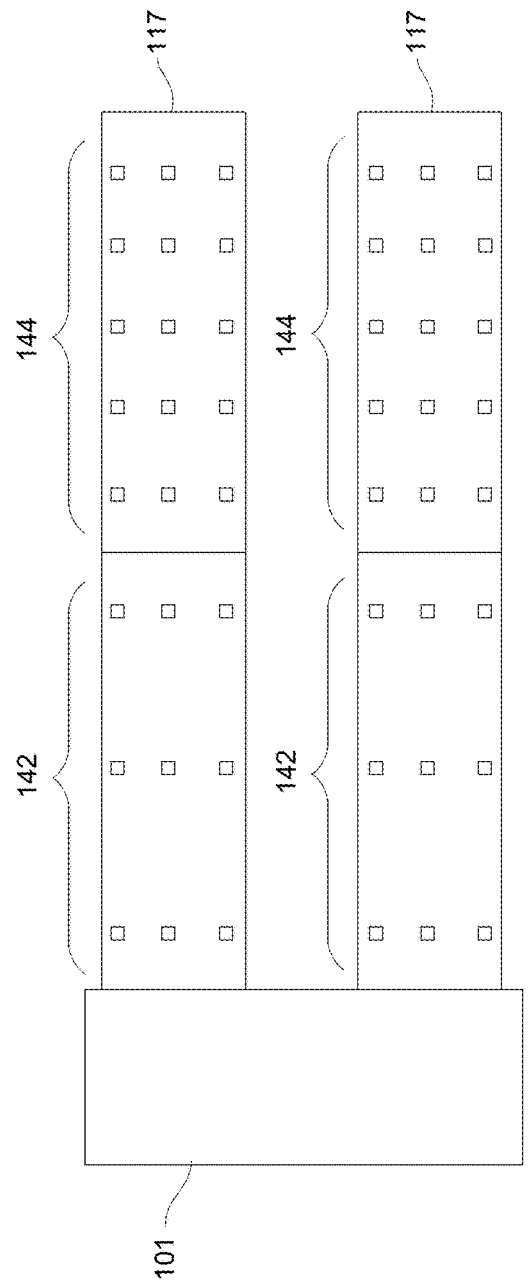

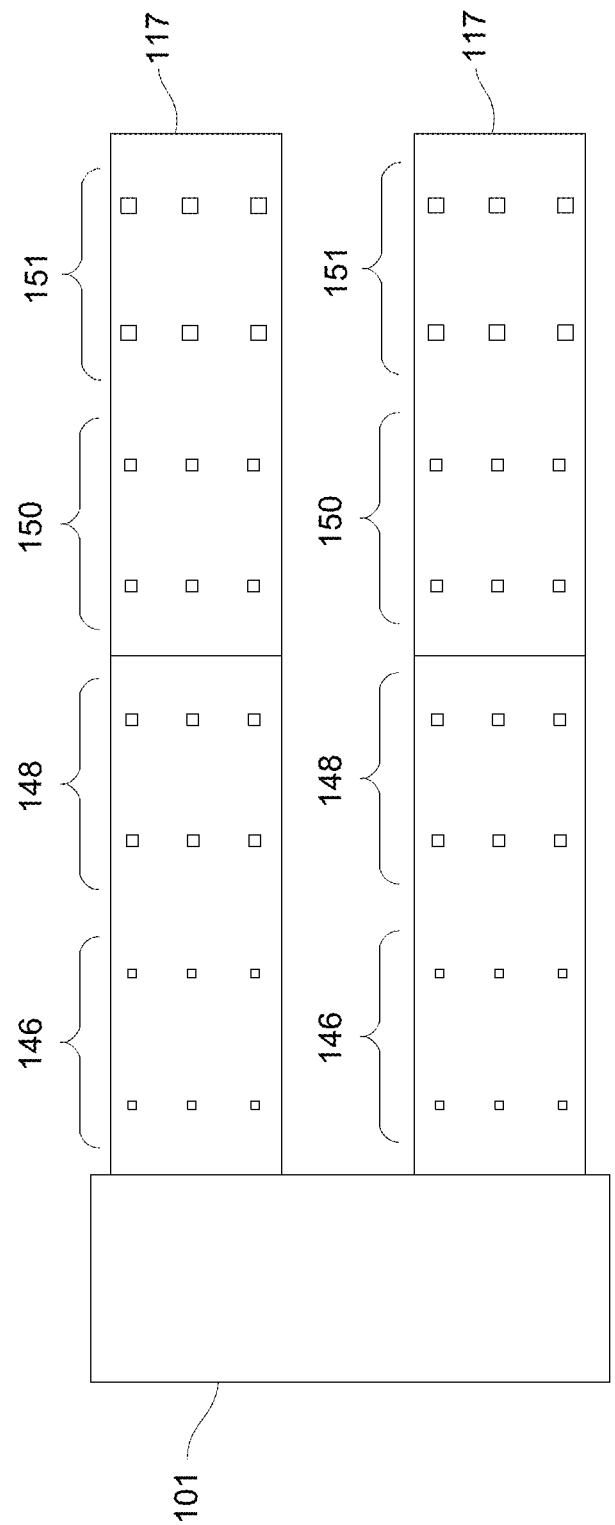

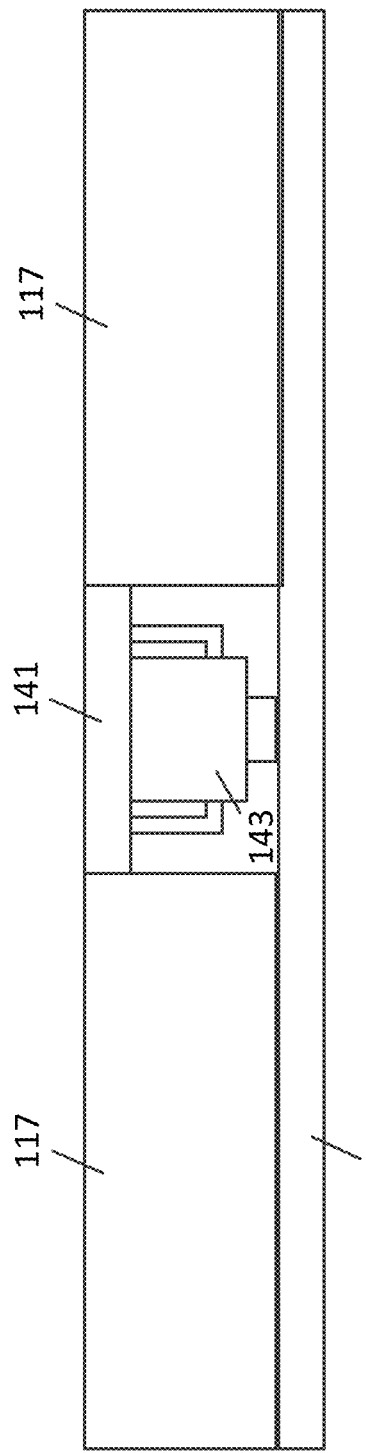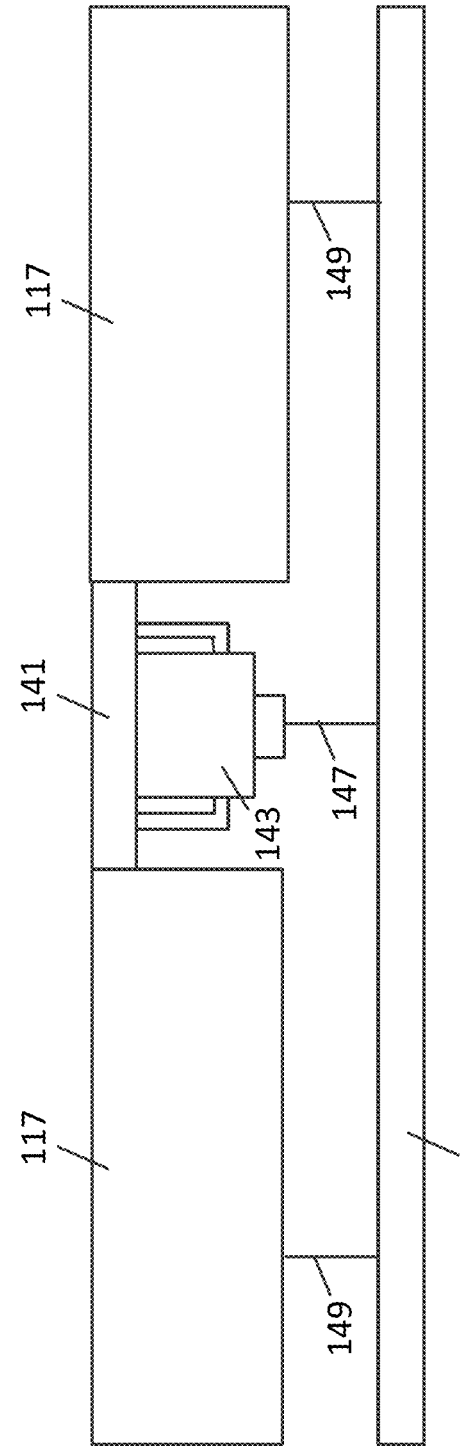

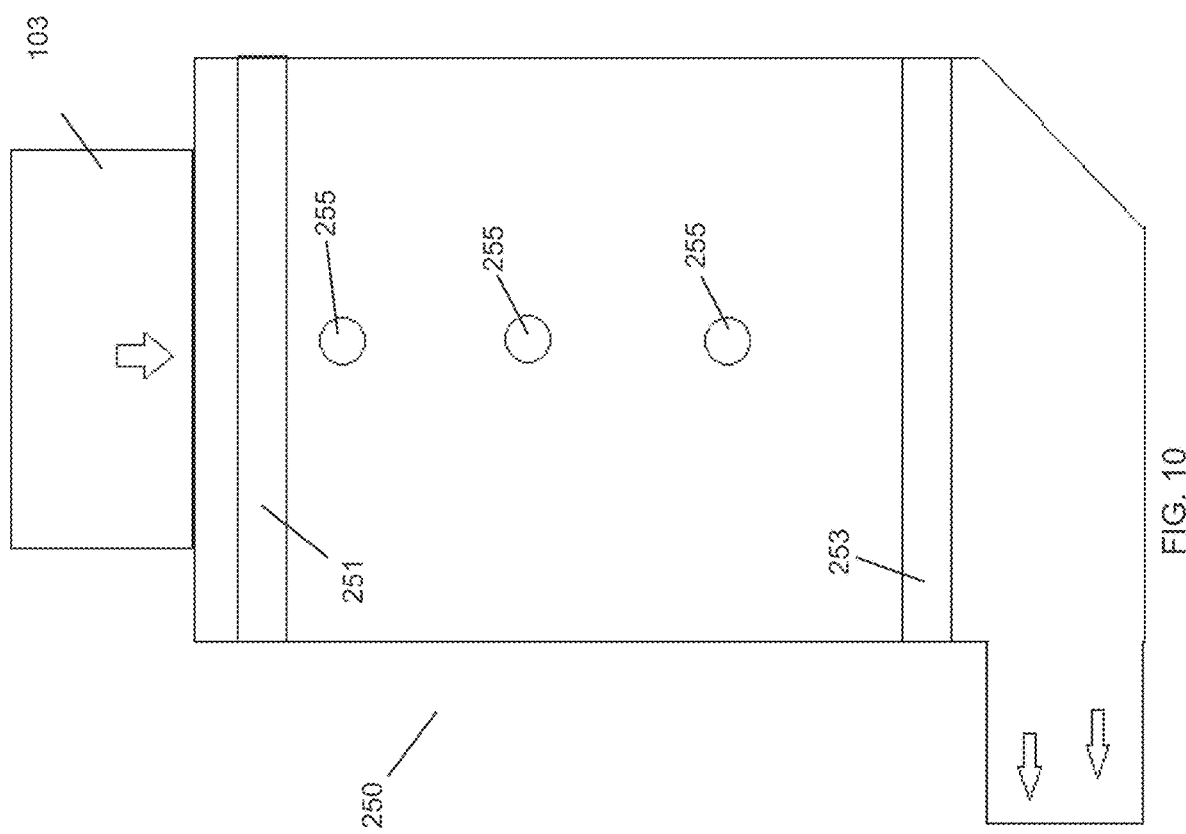

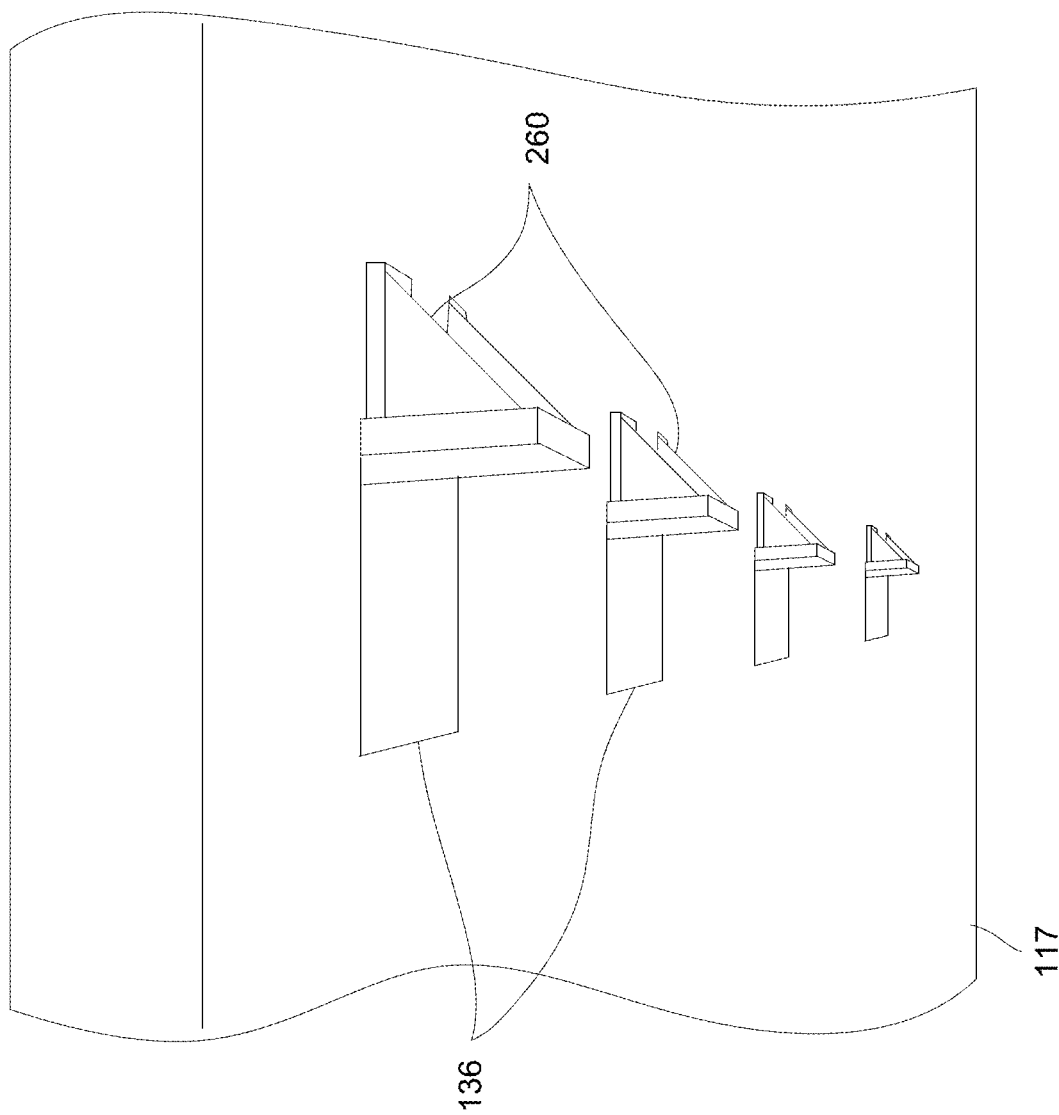

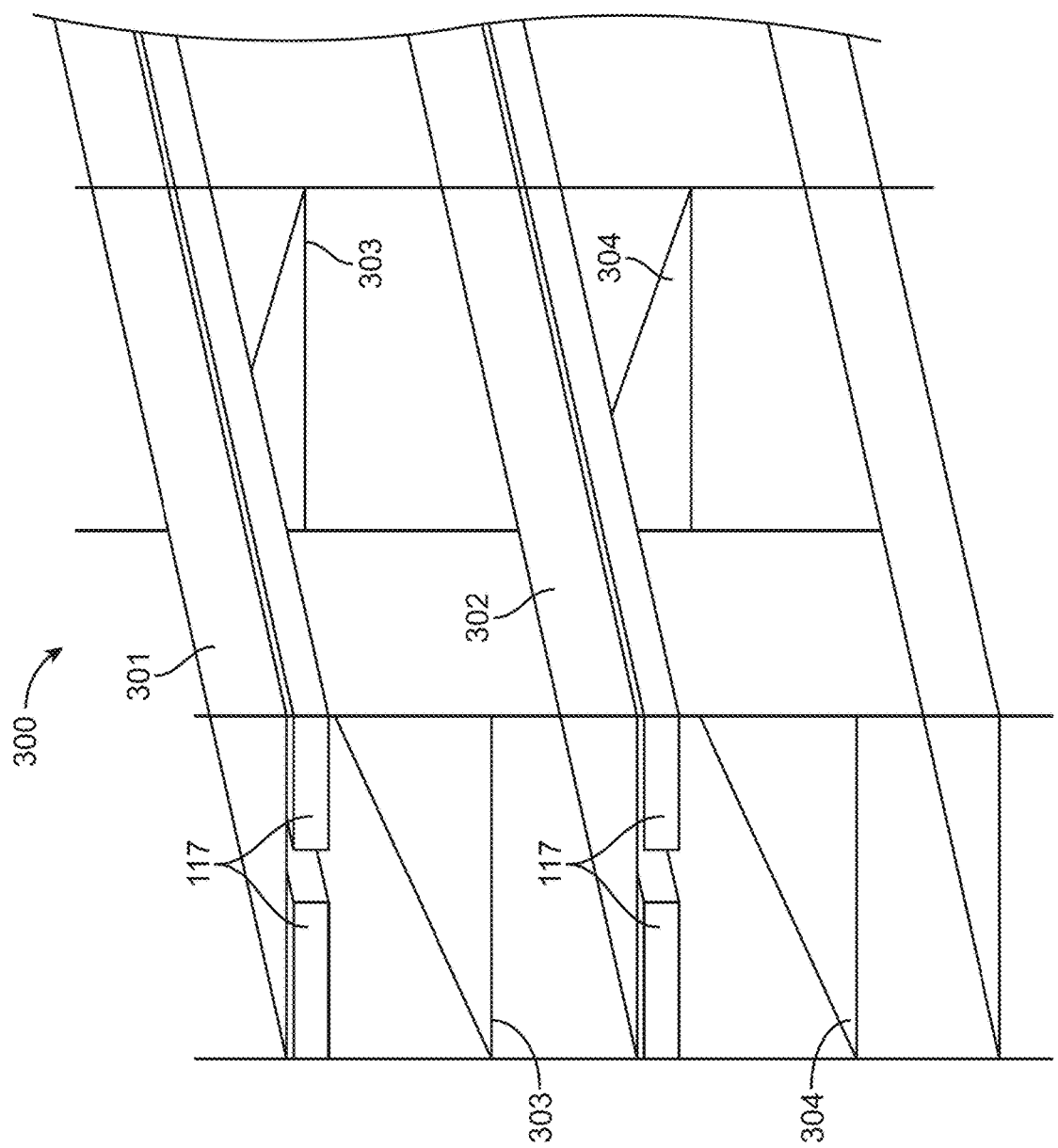

SYSTEM AND METHOD FOR PROVIDING CARBON DIOXIDE AND CIRCULATING AIR FOR A VERTICAL GARDENING SYSTEM

CROSS REFERENCE TO RELATED APPLICATIONS

This application is a continuation-in-part of U.S. patent application Ser. No. 15/730,659, filed Oct. 11, 2017 which claims priority to U.S. Provisional Patent Application No. 62/549,919 filed Aug. 24, 2017; this application further claims the benefit of priority to U.S. Provisional Patent Application No. 62/549,919 filed Aug. 24, 2017 and U.S. Provisional Patent Application No. 62/712,675 filed Jul. 31, 2018. The contents of each application are hereby incorporated by reference.

BACKGROUND OF THE INVENTION

Vertical farming is the practice of producing food and medicine in vertically stacked layers, vertically inclined surfaces and/or integrated in other structures such as warehouses and other structures that can accommodate growing plants. Vertical farming use indoor farming techniques and controlled-environment agriculture (CEA) technology, where all environmental factors can be controlled. These facilities utilize artificial control of light and watering. Prior methods for circulating air are accomplished using wall mounted oscillating fans and ceiling mounted HVAC systems. However, this air circulation method is ineffective in a vertical growing configuration and most vertical gardens are too compact for these environmental control methods to be efficient.

Prior methods for carbon dioxide dispersion use piping a plastic line to the back of a wall mounted fan or a carbon dioxide generator mounted at the ceiling in the room. Both methods do not allow for a controlled direction of carbon dioxide. Prior methods of filtering air have been through large "can filters" attached to a fan on the intake side. However, these large can filters occupy a large volume of space.

Prior methods are also generally silent on transpiration of the plants subjected to air circulation. Transpiration is the process of water movement through a plant and its evaporation from aerial parts, such as leaves, stems and flowers. Water is necessary for plants but only a small amount of water taken up by the roots is used for growth and metabolism. The remaining 97 to 99.5% is lost by transpiration and guttation. Leaf surfaces are dotted with pores called stomata, and in most plants they are more numerous on the undersides of the foliage. The stomata are bordered by guard cells and their stomatal accessory cells (together known as stomatal complex) that open and close the pore. Transpiration occurs through the stomatal apertures, and can be thought of as a necessary "cost" associated with the opening of the stomata to allow the diffusion of carbon dioxide gas from the air for photosynthesis. Transpiration also cools plants, changes osmotic pressure of cells, and enables mass flow of mineral nutrients and water from roots to shoots. Water vapor is removed quickly by air movement, speeding up diffusion of more water vapor out of the leaf. However, if there is no wind, the air around the leaf may not move very much, raising the humidity of the air around the leaf. Wind will move the air around, with the result that the more saturated air close to the leaf is replaced by drier air.

What is needed is system which improves the circulation of air, improves the distribution of carbon dioxide, uses smaller filters that occupy less space, as well as improves transpiration.

SUMMARY OF THE INVENTION

The present invention is directed towards a system and method for circulating air and carbon dioxide and providing light to a vertical gardening system. Traditional methods of wall mounted fans do not properly circulate air. The present invention eliminates the problem of stagnant air pockets created in indoor vertical farming where space is limited. The present invention also disburses carbon dioxide directly onto each row of crops growing on a different shelf of a rack assembly. This process insures that each plant receives an equal quantity of carbon dioxide, as opposed to common methods of releasing carbon dioxide into a large general area with non-uniform distribution. The invention also provides a compact air filtration system, eliminating the need for large can filters commonly used.

The new invention differs from traditional methods by having the filters on the supply side of an air circulation system. This allows for the air coming out of the fan to be disrupted, eliminating the spiral motion and pressurizes the low profile duct evenly on either side. The inventive system creates air movement inside each rack of plants where wall fans can't reach and space does not allow for. The new invention allows carbon dioxide to be plumbed into the plenum and dispersed directly to the plants. The new invention utilizes fan or fans with a filter to clean the air as well as circulating the air. This allows for less space to be used, lower energy costs, and the benefit of being able to change disposable filters more often at a much lower cost than "can filters".

BRIEF DESCRIPTION OF THE DRAWINGS

FIG. 1 illustrates is a side view of an embodiment of the carbon dioxide distribution system.

FIGS. 7C and 7D illustrate bottom views of other embodiments in which the openings may be configured into varied distribution patterns.

FIG. 7E illustrates a bottom view of another embodiment in which the openings may be varied in size along the length of the ducts.

FIG. 8 illustrates a front view of an embodiment of the light ballast, light bar and carbon dioxide distribution ducts.

FIG. 9 illustrates a side view of a rack assembly having a carbon dioxide distribution system, a grow lights system and a carbon dioxide sensor system.

FIG. 10 illustrates a view of a carbon dioxide distribution system on a rack system that includes a plurality of shelves each holding a plurality of plants.

FIG. 12A illustrates one embodiment of a flow diverter attached to or positioned into proximity of the openings.

FIG. 16 shows a perspective view of a distribution system integrated directly with the rack.

DETAILED DESCRIPTION OF THE INVENTION

Figure 2A:
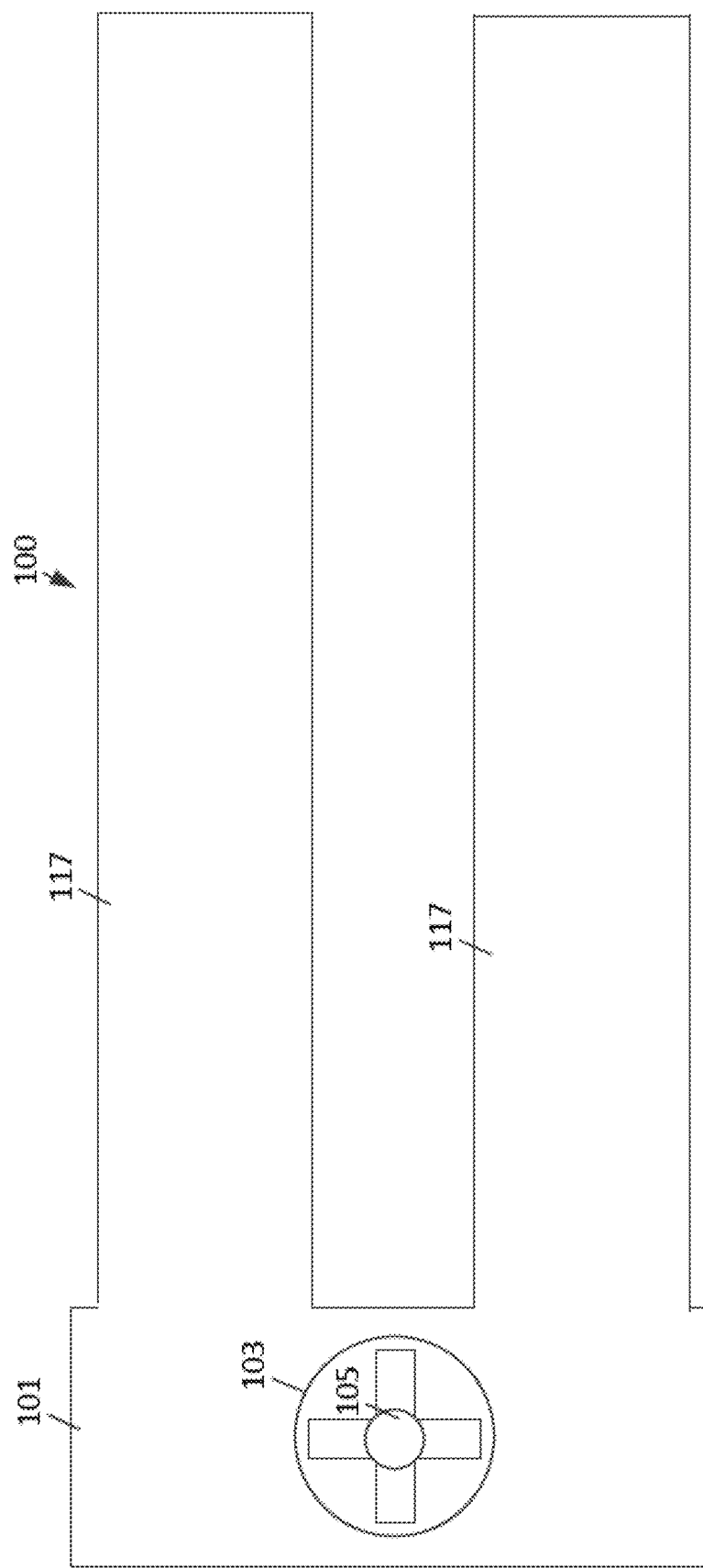
FIG. 2A illustrates a top view of an embodiment of the carbon dioxide distribution system.

The inventive system can be used with a vertical plant growing system to disperse carbon dioxide gas to a plurality of stacked shelves that are arranged vertically in a rack placed in a room or a building. A carbon dioxide distribution system can be mounted over each shelf of the rack so several carbon dioxide distribution systems can be used with each rack. The carbon dioxide distribution system can perform various functions including: circulate air around each of the plants, provides an even distribution of carbon dioxide to each of the plants and filters the recirculating air. A lighting system can also be attached to the bottom of the carbon dioxide distribution system that can provide continuous grow light exposure to the plants.

With reference to FIG. 1, a side view of an embodiment of the carbon dioxide distribution system 100 is illustrated and with reference to FIG. 2, a top view of an embodiment of the carbon dioxide distribution system 100 is illustrated. Air can be directed into an intake collar 103 mounted on an inlet portion of a filter housing 101. In an embodiment, a fan 105 can be used to push the air into the intake collar 103. The air can enter the filter housing 101 and flow through one or more filters 111. The filtered air can then flow into a plenum. A carbon dioxide gas inlet 113 can be coupled to the plenum and the carbon dioxide can be mixed with the filtered air. The carbon dioxide and air mixture can then flow into one or more elongated ducts 117. Each duct 117 has a plurality of holes or openings 102 on a lower surface and the end of the duct 117 can be sealed with an end cap. The holes or openings 102 are described in greater detail below. The elongated ducts 117 are positioned above a plurality of plants on each shelf of the rack assembly. The carbon dioxide and air flow through the holes or openings 102 and onto the plants, which absorb the carbon dioxide.

With reference to FIG. 2A, in an embodiment, the fan 105 can be a 10" or a 6" to 14" inline fan 105 that can be mounted in the intake collar 103 at the top of the filter housing 101, as shown in the top view of the distribution system 100. The inventive system can be used with various types of vertical rack systems with plants positioned on each shelf of the rack system. The fan 105 can be mounted outside of the pallet rack volume on an end of the pallet rack. In an embodiment, the fan 105 flow rate can output 1,000 cubic feet per minute (CFM). In other embodiments, any other airflow mechanism can be used with the carbon dioxide distribution system to drive air through the system. As shown, two ducts 117 may be fluidly coupled to the filter housing 101 such that they extend in parallel relative to one another. However, a single duct may also be used or more than two ducts may be aligned relative to one another. Moreover, while the ducts 117 are shown in the top view as having a rectangular shape, other configurations may potentially be utilized.

Many conventional distribution systems utilize multiple fans due to uneven air distribution over a plant canopy. In a typical example, two 75 W fans may be placed every eight linear rack feet along a row of crops so that a 32 foot rack would utilize eight fans total resulting in a total of 600 W of power usage. The distribution system described herein may utilize a single fan, e.g., 242 W, for the same 32 foot rack. The same configuration may be applied to longer rack lengths. For instance, a conventional fan configuration for a 40 foot rack would require ten fans, a 48 foot rack would require twelve fans, and a 64 foot rack would require sixteen fans. However, each of the increased rack lengths could utilize a single fan with the distribution systems as described herein resulting in reduced power usage and lower costs.

Figure 2B:
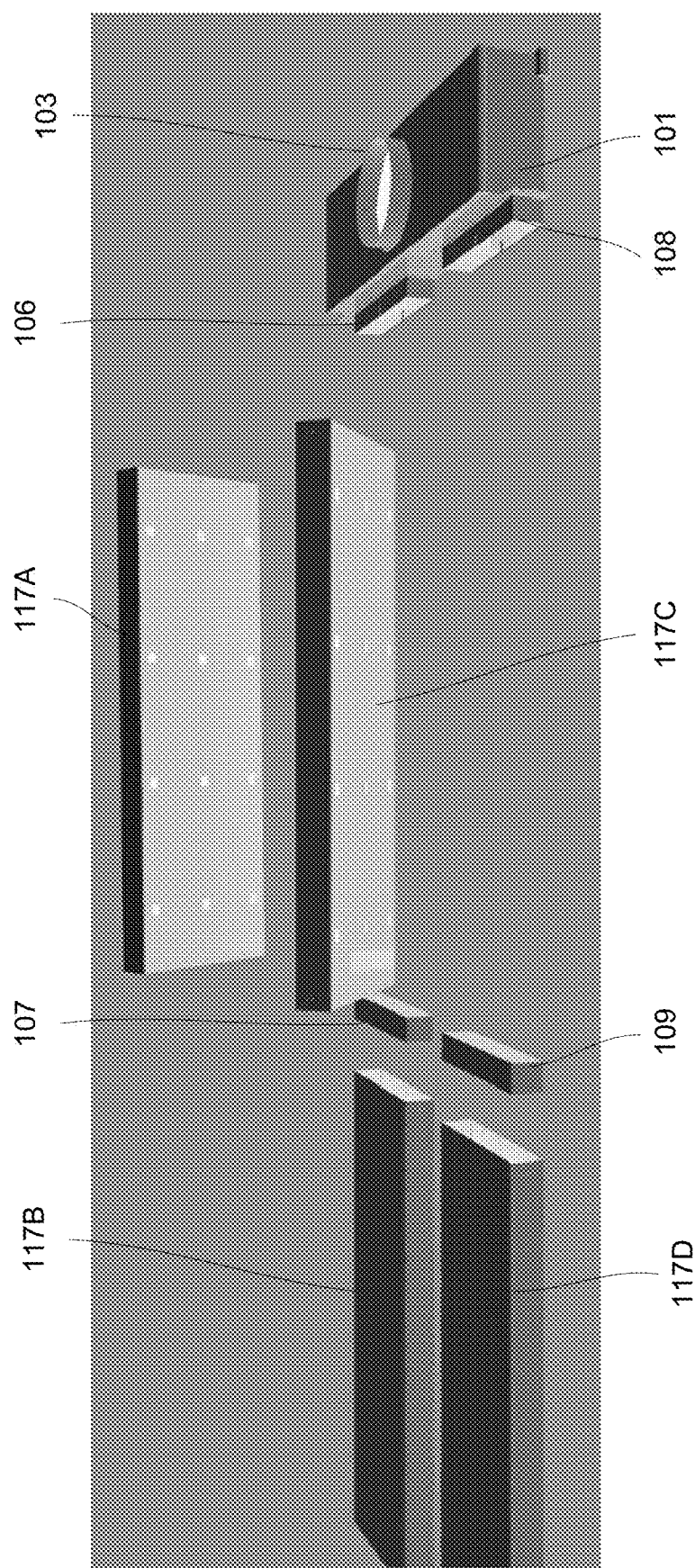
FIG. 2B illustrates a perspective exploded assembly view of a distribution system.
Figure 2C:
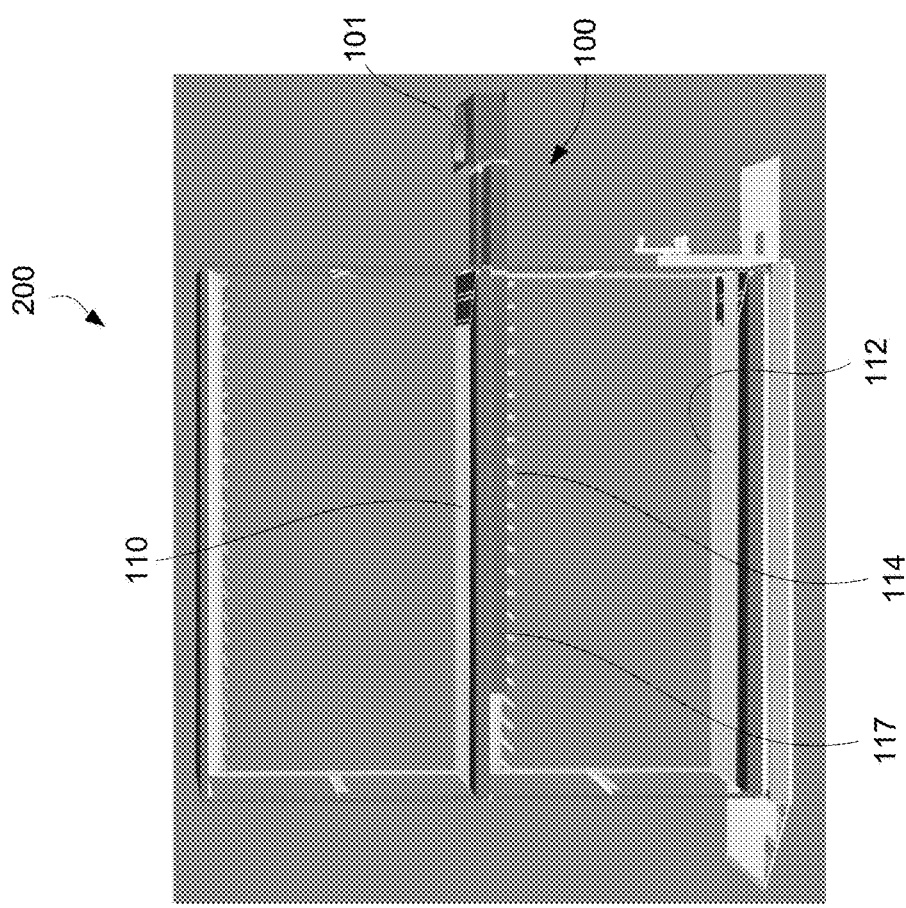
FIGS. 2C and 2D illustrate perspective views of a distribution system integrated within a rack system.
Figure 2D:
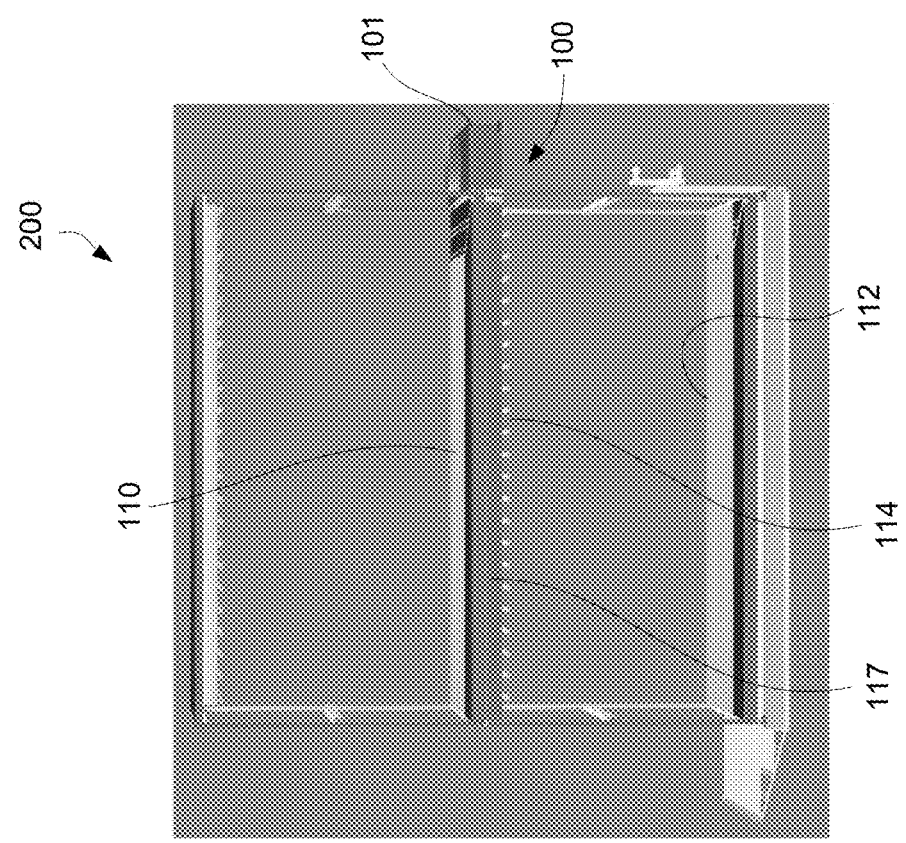

FIG. 2B shows a perspective exploded assembly view in an example of how one embodiment of the distribution system may be assembled. Each of the ducts 117 may be formed from components 117A, 117B and 117C, 117D which may be fluidly coupled to one another via connectors 107, 109. The ducts 117 may then be fluidly coupled to the filter housing 101 via coupling 106, 108, as shown. With the distribution system assembled, they may be slid or urged into place within, e.g., a pallet rack system 200 having one or more shelves (described in further detail herein), as shown in the perspective views of FIGS. 2C and 2D. The illustrations show how one assembled distribution system 100 may be attached below a first shelf 110 so that the air and/or carbon dioxide may be distributed from the duct 117 and onto any plants which may be placed upon a second shelf 112 located below the first shelf 110 and duct 117. With the distribution system secured upon the rack 200, the filter housing 101 may be positioned to extend from the rack 200 to allow for positioning of the fan and access to the filter housing 101.

The distribution system may be attached via one or more structural elements 114 such as braces, retaining brackets, etc. which allow for the distribution system to be slidingly secured or removed from the rack system 200, as shown. If desired, a second distribution system may be secured to the top of the rack system 200 so that air and/or carbon dioxide may be distributed upon any plants placed upon the first shelf 110 below the second distribution system.

The shelves in any of the embodiments described herein may vary in the number of shelves utilized per rack and may also vary in size. For example, one variation of the one or more shelves may each range in length from, e.g., 8 ft. to 64 ft., and in width from, e.g., 2 ft. to 4 ft. Various configurations of the shelf may range, e.g., 4 ft.×8 ft.; 3 ft.×8 ft.; 2 ft.×8 ft.; 4 ft.×4 ft.; 4 ft.×3 ft.; 4 ft.×2 ft., etc.

Additionally, the vertical distance between each shelf of a rack may be adjusted depending upon various factors, e.g., desired number of shelves or spacing between each shelf, growth phase of plant, etc. For instance, the distance between each shelf may be varied from, e.g., 12 in. to 48 in. when the plants are in their vegetative cycle, 36 in. to 96 in. when the plants are in their flower cycle, etc.

The racks as well as shelves may be constructed from various materials, e.g., powder coated square steel, aluminum, etc. Additionally and/or alternatively, one or more of the shelves may be configured to define a slope towards one specified corner or edge relative to horizontal for facilitating drainage of water or other liquids from the plants positioned upon the shelves.

Figure 2E:
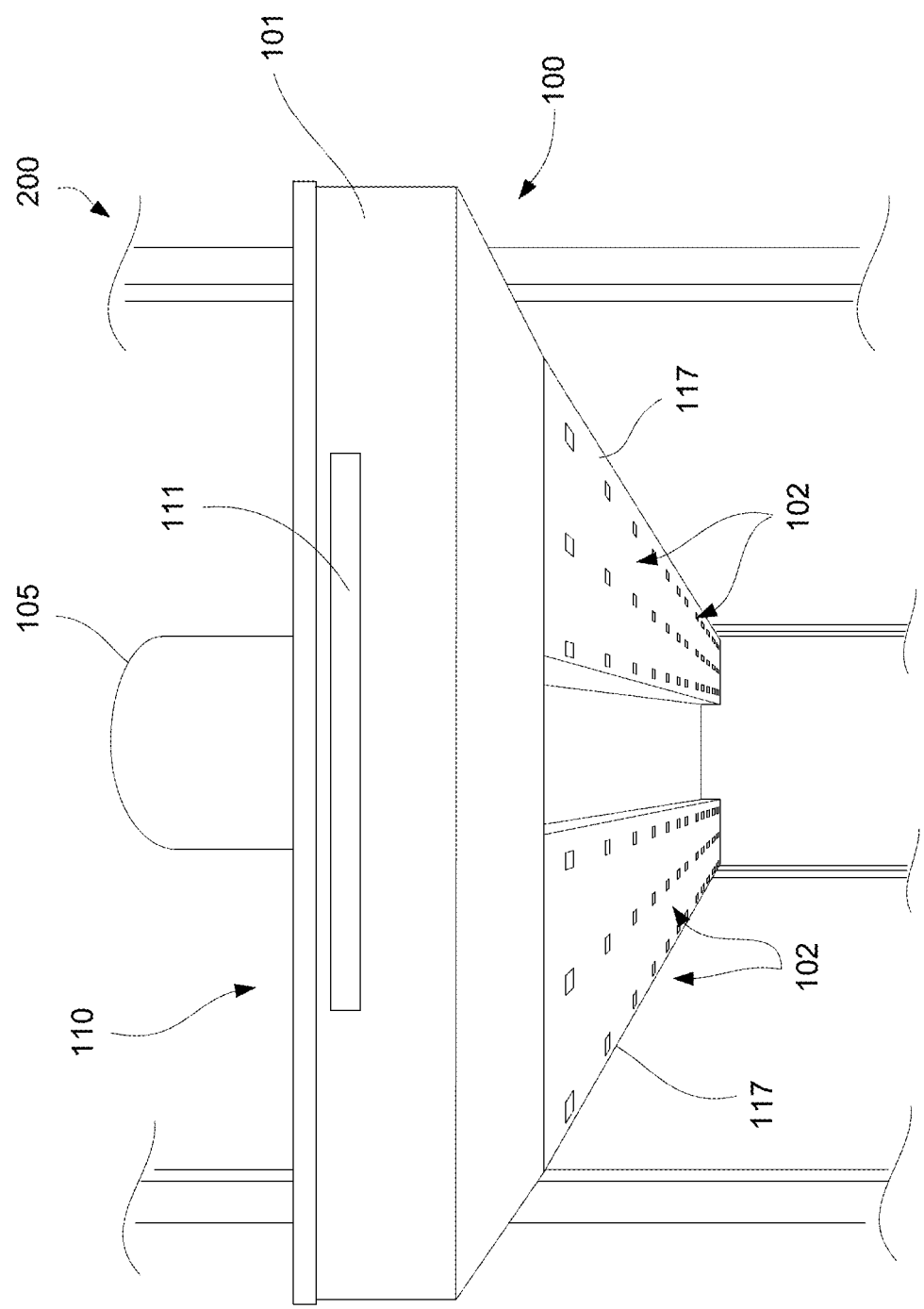
FIG. 2E illustrates an perspective end view of a distribution system when secured upon a rack system.

FIG. 2E shows a perspective end view of another embodiment in which the distribution system has been secured below a shelf 110 of the rack 200. As illustrated with the filter housing 101 and fan 105 extending from the rack 200, the two parallel ducts 117 may be seen extending from the filter housing 101 and along the length of the rack with the plurality of openings 102 aligned along the bottom surface of the ducts 117 for distributing air and/or carbon dioxide upon any plants positioned beneath.

Figure 2F:
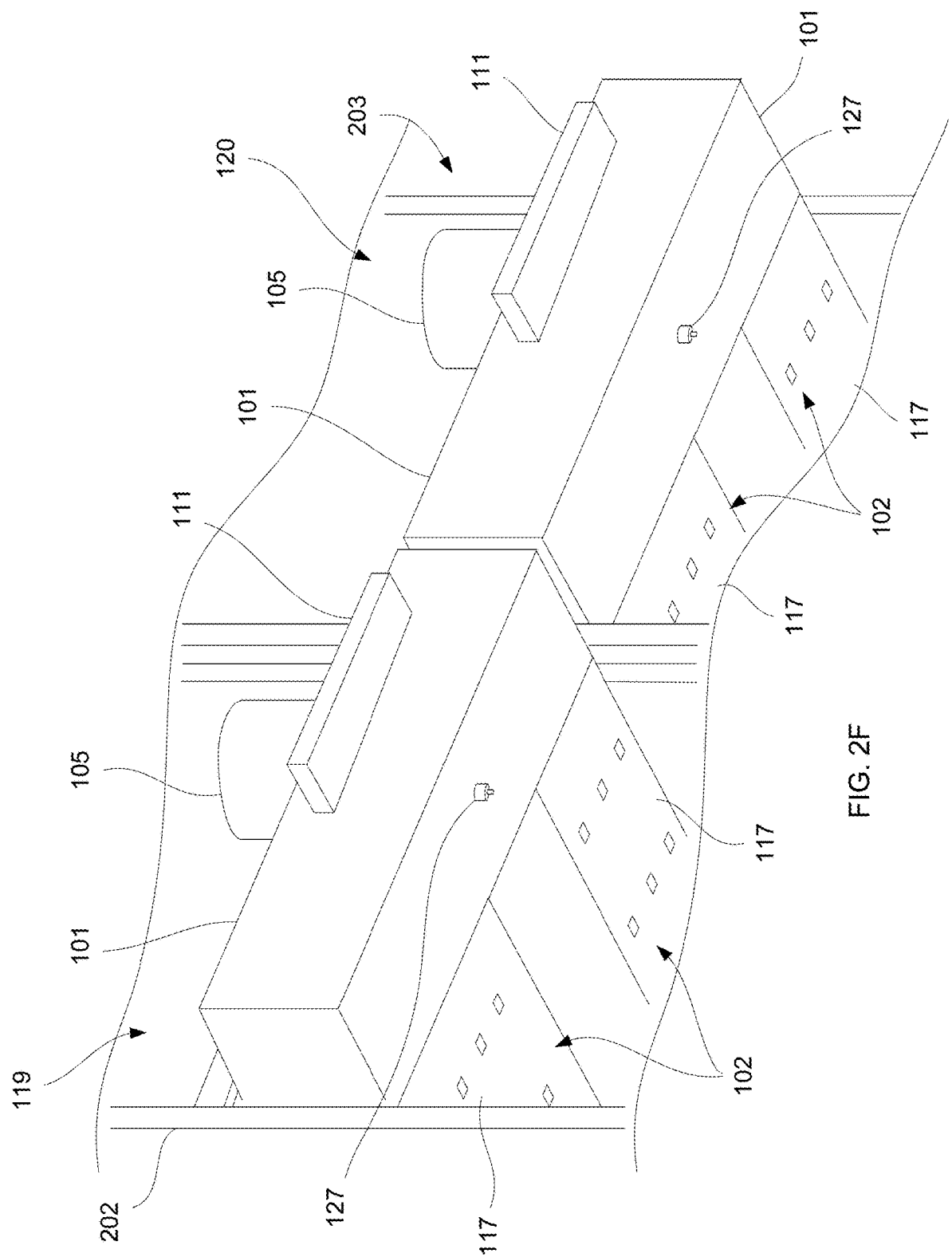
FIG. 2F illustrates a perspective view of multiple distribution systems secured to multiple racks.

FIG. 2F shows a perspective view of another embodiment in which multiple distribution systems may be utilized with multiple racks positioned adjacent to one another. In this example, a first distribution system 119 may be seen secured to a first rack 202 with a second distribution system 120 secured to a second rack 203 adjacent to the first rack 202. Any number of distribution systems may be utilized with any number of racks depending upon the desired configuration.

Figure 2G:
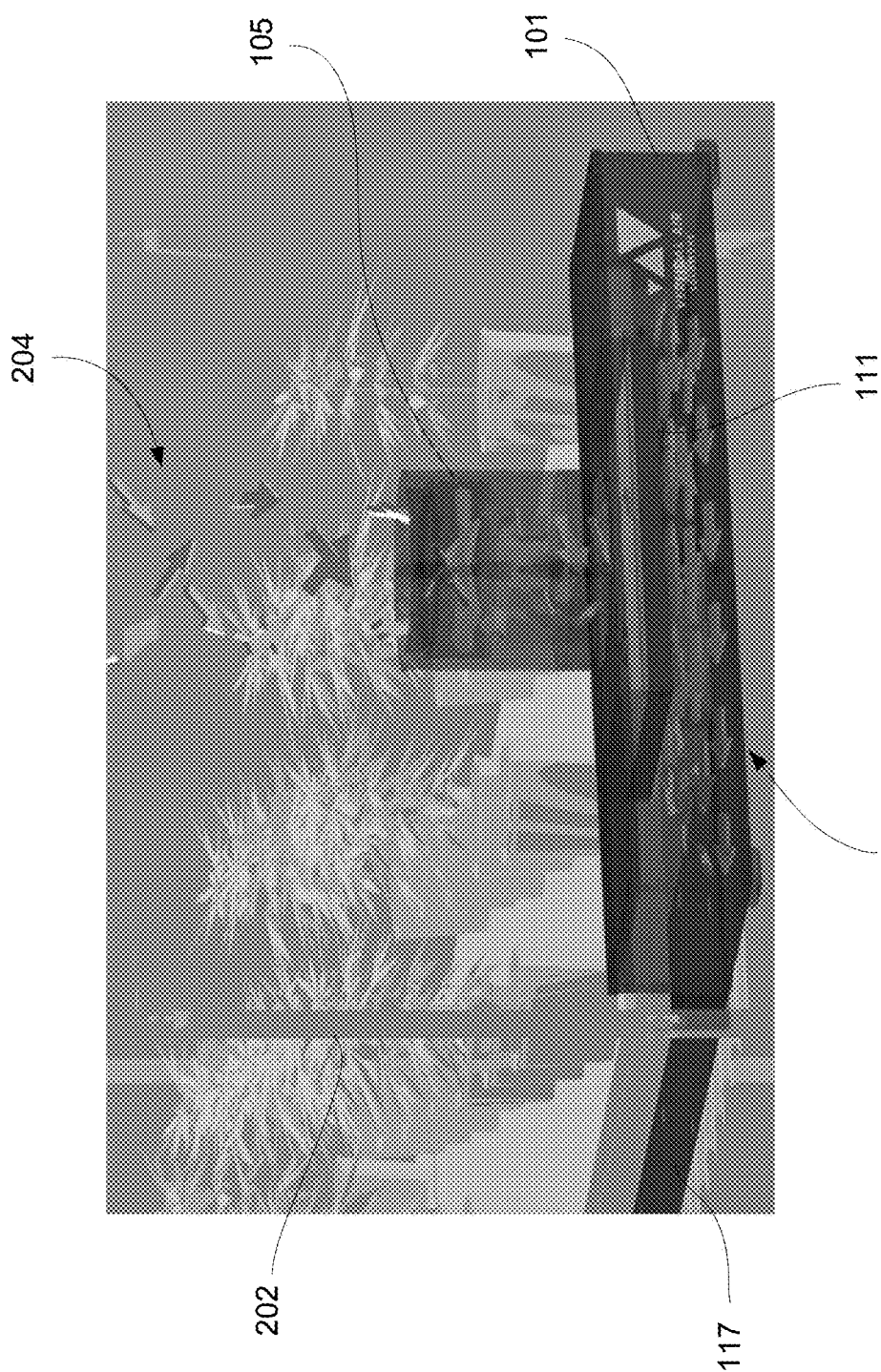
FIG. 2G illustrates a perspective view of a fan drawing air into the filter housing of a distribution system.

FIG. 2G illustrates a perspective view of how the fan 105 may be used to draw air 204 into the filter housing 101. The air may be provided via ambient air drawn into the fan 105 or via tubing or ducting fluidly coupled to the fan 105 where the air (or other gas) may be drawn from another location or reservoir. With the air 204 drawn into the fan 105, through the filter 111, and into the filter housing 101, the air 204 may be optionally mixed with carbon dioxide (or any other gas) and the mixture 205 may be conveyed through the ducts 117 for distribution.

Figure 3:
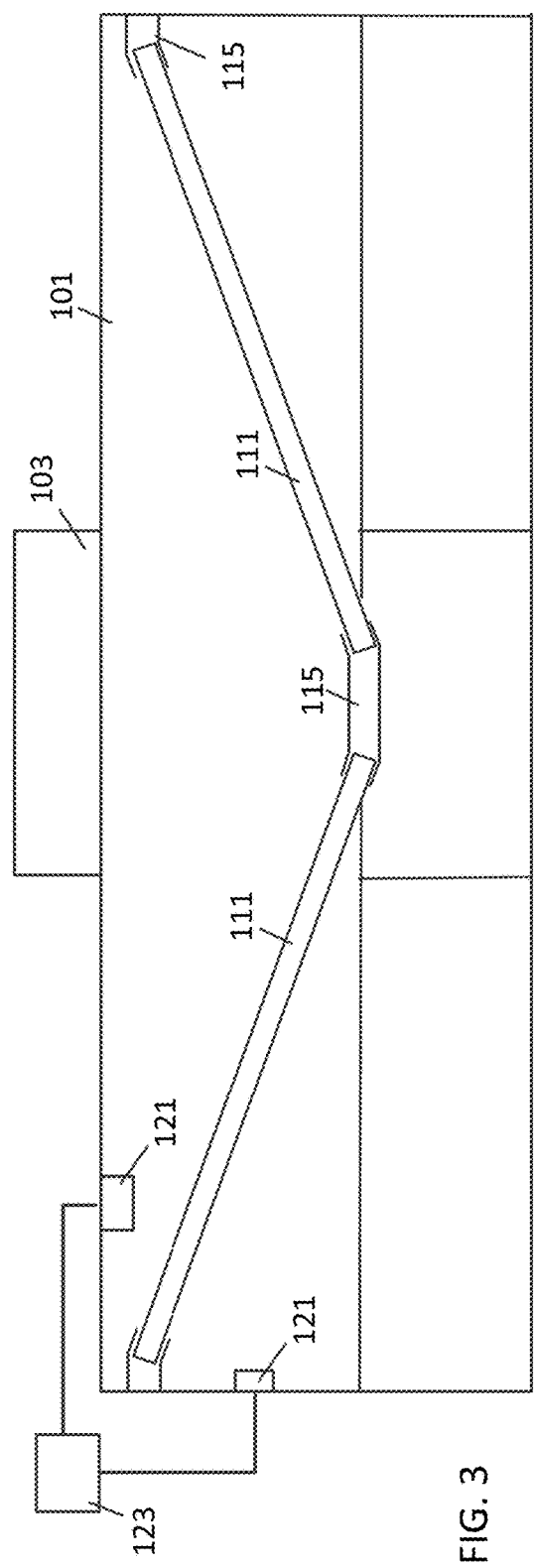
FIG. 3 illustrates a front section view of an embodiment of the air intake portion of the carbon dioxide distribution system.
Figure 4:
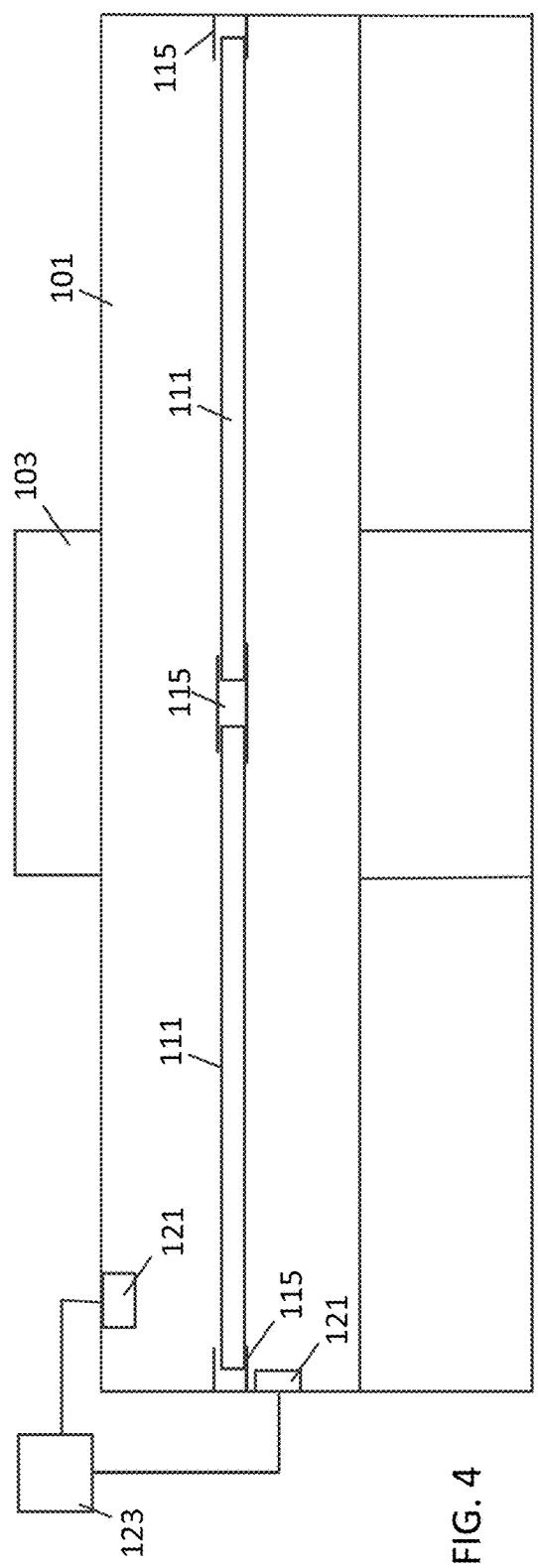
FIG. 4 illustrates a front section view of another embodiment of the air intake portion of the carbon dioxide distribution system.
Figure 5:
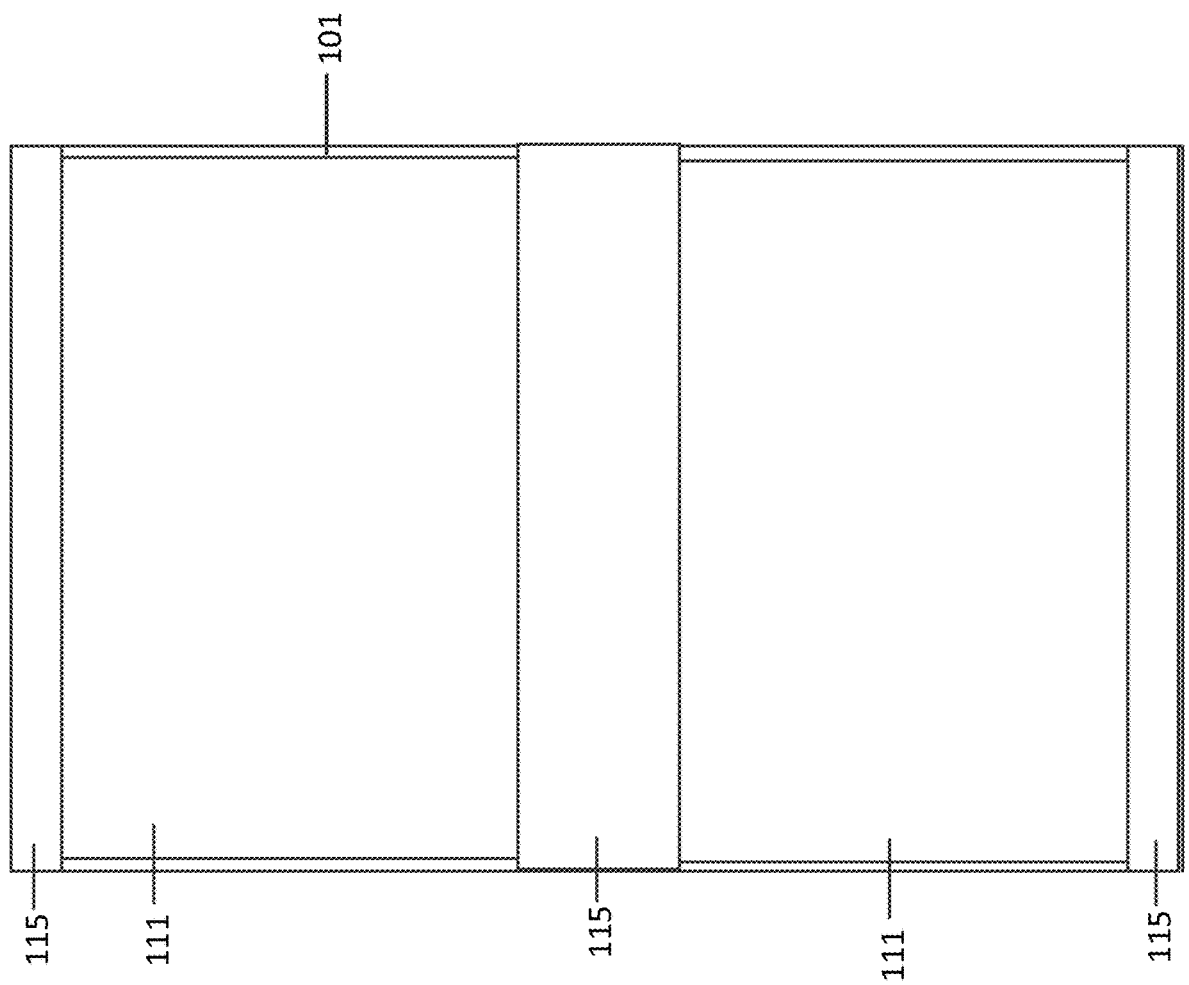
FIG. 5 illustrates a top section view of an embodiment of the air intake portion of the carbon dioxide distribution system.

With reference to FIG. 3, a cross section front view of an embodiment of the filter housing 101 is illustrated. In this embodiment, there are two filters 111 that are held in angled positions by channel brackets 115. With reference to FIG. 4, another cross section front view of an embodiment of the filter housing 101 is illustrated. In this embodiment, there are two filters 111 that are held in flat positions by the channel brackets 115. Air flows through the center portions of the filters 111 so the brackets 115 only contact the edges of the filters 111. In other embodiments, the filters 111 can be held by any other holding mechanisms. With reference to FIG. 5 a top sectional view of an embodiment of the filter housing 101 illustrated. A fan can be mounted within the intake collar 103 which can be attached to the air inlet on top of the filter housing 111. The fan can blow air into the filter housing 101 and through the filters 111.

With reference to FIGS. 3-5, the filters 111 can be mounted across the width of the filter housing 101 so that air from the inlet must flow through one of the filters 111. In this example, a first filter 111 is on one side of the filter housing 101 and a second filter 111 is on an opposite side of the filter housing 101. In an embodiment with reference to FIG. 3, the filters 111 can be angled rather than horizontally oriented within the filter housing. The edge of the filters 111 at the center of the filter housing 101 can be lower than the edges of the filters 111 at the outer sides of the filter housing 101. The filters 111 can be mounted on support structures which can be channel brackets 115 that extend across the length of the filter housing 101. In an embodiment, the support structures channel brackets 115 can have grooves that securely hold the inner and outer edges of the filters 111 in place within the filter housing 101. The filter housing 101 can have a hinged door that can be open to access the filters 111. The filters 111 can be removed and replaced when the hinged door is opened and the filters 111 can be locked in place within the filter housing 101 when the hinged door is closed.

The filters 111 can trap particulates from the plants, which can be beneficial when the plants being grown are very aromatic. Terpenes are a group of organic molecules derived from isoprene that are present in fruits, vegetables and vegetation. Terpenes are derived biosynthetically from units of isoprene and the basic molecular formula is $(C_5H_8)$. These terpenes cause the specific odors for example: limonene in citrus fruit, pinene in pine tree. Marijuana is also a plant that produces terpenes. Because the smell of terpenes can be a nuisance to the surrounding areas, it can be highly beneficial to remove the marijuana terpenes that have been released into the air by the cannabis plants. In an embodiment, the filters used with the system can be terpene filters that remove terpenes from the circulating air in the plant grow building. By removing terpenes from the air, the odor generated by the building where the plants are grown can be greatly reduced so that the building is not a nuisance to the surrounding community. When the terpenes saturate the filters 111, the door to the filter housing 101 can be opened and the filters 111 can be removed and replaced with clean filters 111. The used filters 111 can be placed in sealed bags so that the odors are contained.

When the air enters the plenum through the fan 105, the air must passes through the air filters 111. In an embodiment, the filters 111 can have the dimensions, 12"×20"×1". This process disrupts the spiraling air flow created by the fan 105 and allows both sides of the supply runs to pressurize and distribute even amounts of air through the 1.125" duct exit holes. This was unachievable with a direct fan to supply run configuration. The process also eliminates the need for a separate fan and carbon filter to be installed in the room.

In an embodiment, a pressure sensor(s) 121 can be mounted in the filter housing 101 to measure static pressure and a differential pressure across the filters 111. This information can be used to determine the flow resistance through the filter 111 and the flow rate through the system. If a first pressure sensor 121 is mounted in the filter housing 101 upstream of the filter 111 and a second pressure sensor 121 is mounted in the filter housing 101 downstream of the filter 111, the differential pressure across the filters 111 can be measured. A clean filter 111 will allow air to more easily flow through the filter 111 and will have a lower differential pressure than a dirty filter 111. In an embodiment the system can have a processor 123 that is coupled to the pressure sensors 121 that monitor the differential pressure and the processor 123 can issue notifications when the differential pressure exceeds a predetermined value. The operator will then know that the filter(s) 111 need to replaced.

In another embodiment, the system sensor 121 and processor 123 can monitor the static pressure of the pressure up stream of the filter 111. This monitoring system can depend upon the air input providing a constant power or flow rate into the system. As the filter(s) 111 becomes dirty, the static pressure upstream of the filter(s) 111 will increase and when the upstream static pressure exceeds a predetermined value, the monitoring system can inform the operator who will then know that the filter(s) 111 need to replaced. Conversely, the system can monitor the static pressure of the pressure down stream of the filter(s) 111. As the filter(s) 111 becomes dirty, the static pressure downstream of the filter 111 will decrease and when the down stream static pressure falls below a predetermined value, the monitoring system can inform the operator who will then know that the filter(s) 111 need to replaced.

Figure 6:
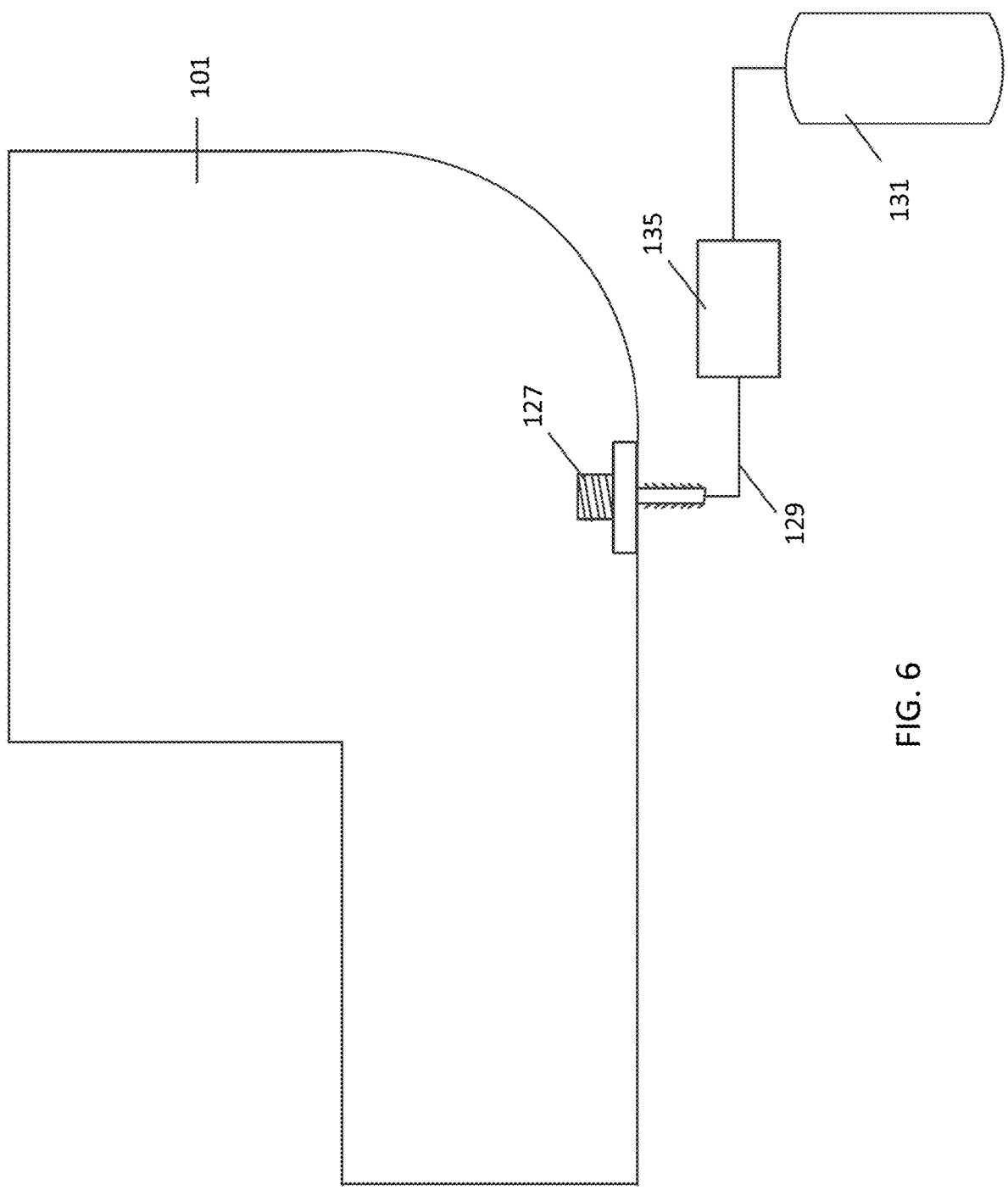
FIG. 6 illustrates a side section view of an embodiment of the air intake portion of the carbon dioxide distribution system.

With reference to FIG. 6, a side sectional view of the filter housing 101 is illustrated showing the carbon dioxide inlet 127 coupling attached to the bottom of the filter housing 101. The carbon dioxide inlet 127 in the illustrated example, can have a threaded insert which is bolted to the inner surface filter housing 101 which forms a seal with the filter housing 101 and prevents carbon dioxide gas leakage. An inlet coupling 127 extends from the filter housing 101. In an embodiment, the inlet coupling 127 can be a nipple which can be coupled to tubing 129 that can be used to deliver carbon dioxide to the filter housing 101. The carbon dioxide inlet coupling 127 can be coupled with tubing 129 to a carbon dioxide gas source 131 such as a carbon dioxide tank or other carbon dioxide supply. In an embodiment, a control valve 135 can be coupled between the carbon dioxide gas source 131 and the filter housing 101. The control valve 135 can be coupled to a carbon dioxide controller, which can monitor the carbon dioxide levels in the building or at the plant levels. The carbon dioxide controller can maintain a predetermined carbon dioxide level by decreasing the carbon dioxide flow when the detected carbon dioxide level is too high and increase the carbon dioxide flow when the detected carbon dioxide level is too low.

Figure 7A:
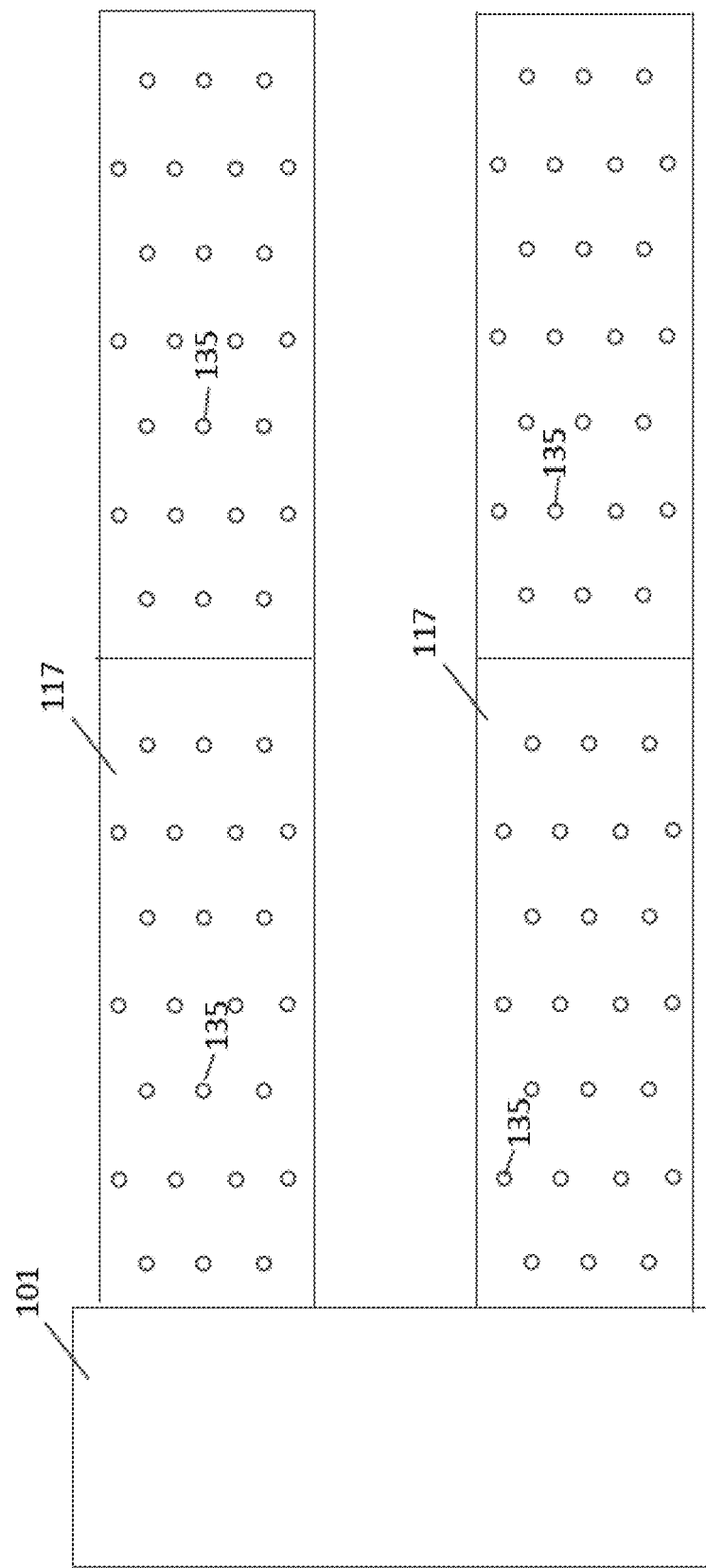
FIG. 7A illustrates a bottom view of an embodiment of the carbon dioxide distribution system.

With reference to FIG. 7A, a bottom view of an embodiment of distribution ducts 117 of the carbon dioxide distribution system 100 is illustrated. Air and carbon dioxide flow through the ducts 117 from the proximal end attached to the filter housing 101 to the distal end of the ducts 117. The air and carbon dioxide will flow out of the holes or openings 135 on the bottom of the ducts 117. In an embodiment, the holes 135 can be 1.125 inch diameter holes. However, in other embodiments, the holes or openings 135 can be any suitable size such as 0.5 inch to 2.0 inch diameters. In addition, while the holes or openings 135 are shown as having an alternating distribution pattern between each adjacent row, the holes or openings 135 may alternatively have a uniform distribution or other distribution pattern, as described further below.

The distribution ducts 117 can be a metal duct system made from aluminum or galvanized sheet metal. The distribution ducts 117 can be designed to be as thin as possible while still providing desired flow rate of carbon dioxide and velocity of air movement over a vertical gardening application. This can be accomplished by using a thin cross section distribution duct 117 so that the ducts consume very little vertical space. For example, the ducts 117 can have a cross section that is about 3 inches high and about 16 inches wide. This height to width (H/W) ratio can be known as the aspect ratio. In this example, the aspect ratio is $3/16 = 0.1875$. In an embodiment, the aspect ratio of the ducts 117 is less than 0.25. The flow rate of the air and carbon dioxide can be quantified with a flow rate metric such as cubic feet per minute (CFM). The carbon dioxide and airflow eliminates warm pockets of air by providing concentrated air movement, carbon dioxide dispersion, and filtration.

Figure 7B:
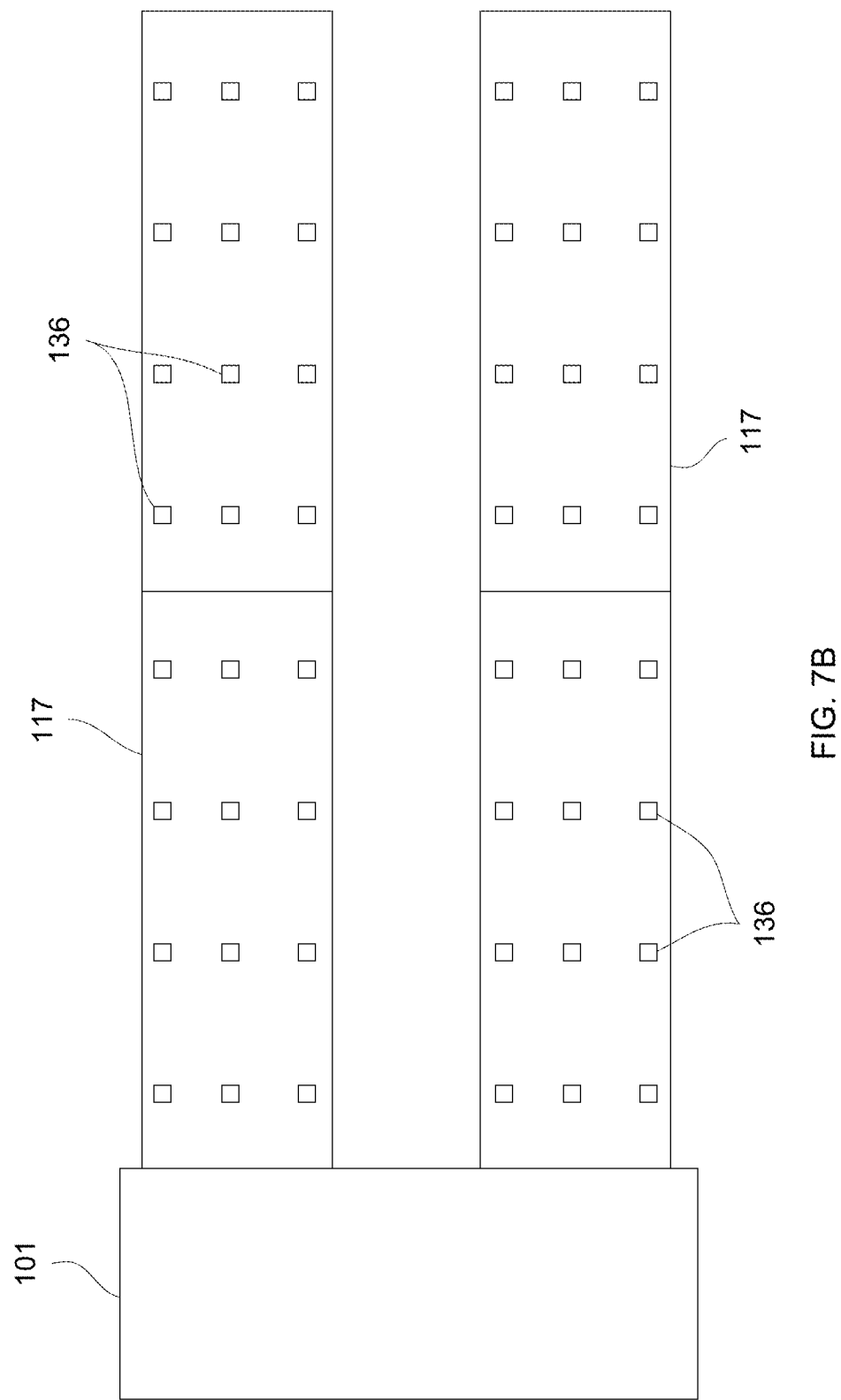
FIG. 7B illustrates a bottom view of another embodiment in which the openings may be configured into rectangular or square openings.

FIG. 7B shows a bottom view of another embodiment of the distribution system which defines a plurality of rectangular or square openings 136 aligned in a uniform distribution pattern along the lengths and widths of the ducts 117. Each of the openings 136 in this variation may range in length (along the direction of the longitudinal axis of the duct 117) and in width (transverse to the longitudinal axis of the duct 117). Additionally, the number of openings 136 may also vary so long as the total area of the openings range as a percentage of the total surface area of the ducts 117 upon which the openings 136 are defined.

As described herein, the fan 105 can be mounted outside of the pallet rack volume on an end of the pallet rack. In one embodiment, the fan 105 flow rate can output 1,000 CFM while in other embodiments, the system may output between, e.g., 5.5 to 8 CFM at a rate of, e.g., 600 to 800 ft/min. The output CFM may be obtained at a distance of, e.g., 4 to 6 inches, above the plant canopy to provide adequate air movement without overstressing the underlying plants. A controller may be used to adjust the volume and velocity depending on, e.g., the distance between the distribution system and the plants. The distribution system and flow rates may be configured so that the flow exiting the openings 136 along the ducts 117 is balanced along the length of the ducts 117. For instance, the flow rate from a proximal location as compared to the flow rate from a distal location along the ducts 117 may vary within, e.g., 1 to 2 CFM, and, e.g., 100-200 ft/min, along racks up to, e.g., 56 feet in length.

With the flow parameters configured with the distribution system, transpiration in plants treated with the distribution system may improve. For instance, a 30 to 40% increase in transpiration may result.

Instead of a uniform distribution pattern, the openings may be defined in alternative patterns. For instance, FIG. 7C shows a bottom view of another embodiment in which the length of the ducts 117 may be separated into increasing numbers of openings for each subsequent region away from the filter housing 101. A first region 138 may define a first number of openings, a second region 139 distal to the first region 138 may define a second number of openings which is greater than the first number, and a third region 140 distal to the second region 139 may define a third number of openings which is greater than the second number of openings. The number of regions and the number of openings defined within each region may be varied depending upon the distribution of the air as well as other parameters such as pressure, flow rates, etc. Additionally and/or alternatively, while the patterns are shown to be identical between each of the adjacent ducts 117, the pattern on the first duct may be different from the pattern on the second duct, if so desired.

FIG. 7D shows another embodiment in which the duct may define a first region 142 having a first uniform distribution of openings, and a second region 144 distal to the first region 142 having a second uniform distribution of openings. In this embodiment, the second region 144 defines the second uniform distribution which is relatively more dense (e.g., having a larger total area of openings) than the first uniform distribution. As discussed above, the number of regions and the number of openings defined within each region may be varied depending upon the distribution of the air as well as other parameters such as pressure, flow rates, etc. Additionally and/or alternatively, while the patterns are shown to be identical between each of the adjacent ducts 117, the pattern on the first duct may be different from the pattern on the second duct, if so desired.

FIG. 7E shows yet another embodiment in which the distribution system defines several regions with uniform distribution of openings but with the openings varying in size so that the total area of the openings increases distally along the length of the ducts. A first region 146 may have a distribution of first openings having a first size. A second region 148 distal to the first region 146 may have a distribution of second openings having a second size which is relatively larger than the first size. A third region 150 distal to the second region 148 may have a distribution of third openings having a third size which is relatively larger than the second size. Likewise, a fourth region 151 distal to the third region 150 may have a distribution of fourth openings having a fourth size which is relatively larger than the third size, and so on. As discussed above, the number of regions and the number of openings defined within each region may be varied depending upon the distribution of the air as well as other parameters such as pressure, flow rates, etc. Additionally and/or alternatively, while the patterns are shown to be identical between each of the adjacent ducts 117, the pattern on the first duct may be different from the pattern on the second duct, if so desired.

Figure 7F:
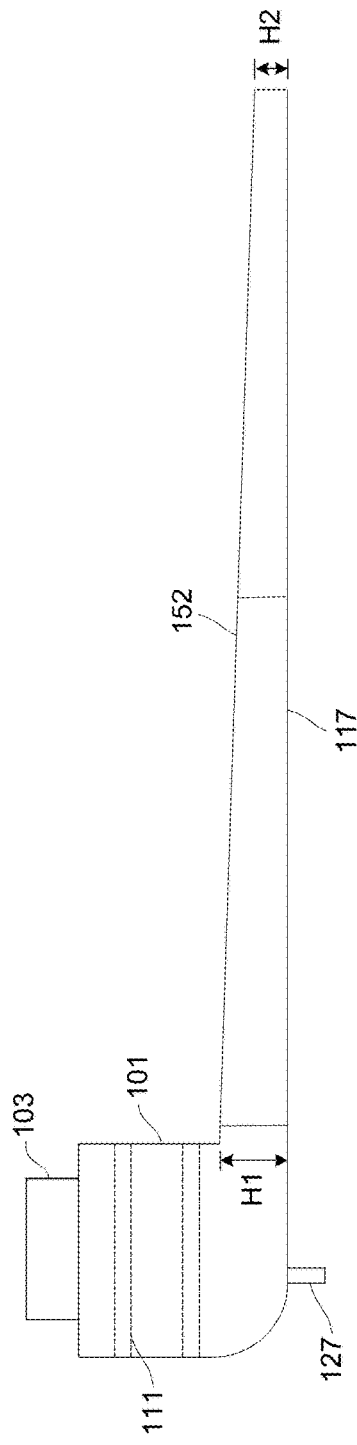
FIG. 7F illustrates a side view of another embodiment in which the ducts may be tapered in height along its length.
Figure 7G:
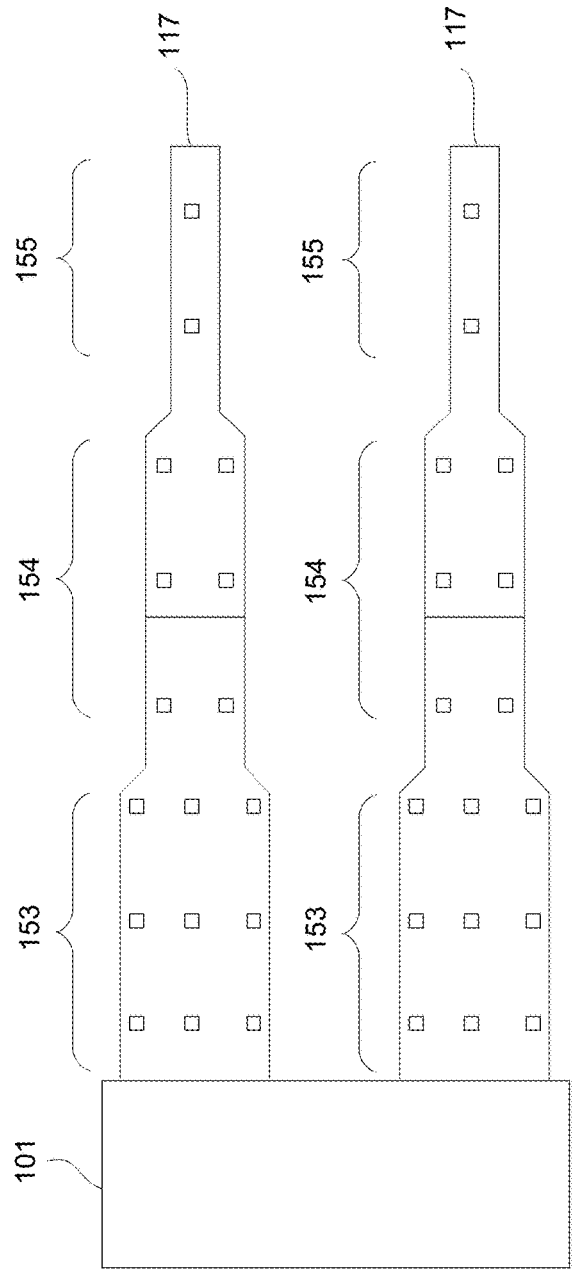
FIG. 7G illustrates a bottom view of another embodiment in which the ducts may be varied in width along its length.

Additionally and/or alternatively, the ducts 117 may also be varied in height to adjust for the parameters such as pressure, flow rates, etc. relative to the length of the duct. FIG. 7F shows yet another embodiment in the side view of a distribution system in which the duct 117 may be tapered or otherwise reduced in height the further distal relative to the filter housing 101. For example, the duct may have a first height H1 where the duct joins the filter housing 101 but the lower and/or upper surface 152 may be tapered such that the ending height H2 of the duct at the distal end may be reduced. Another alternative embodiment is shown in the bottom view of FIG. 7G which illustrates ducts 117 which may be reduced in cross-sectional width the further distal relative to the filter housing 101. The example shown illustrates a first region 153 having a first width, a second region 154 distal to the first region 153 and having a second width which is smaller than the first width, and a third region 155 distal to the second region 154 and having a third width which is smaller than the second width. As discussed above, the number of regions and the number of openings defined within each region may be varied depending upon the distribution of the air as well as other parameters such as pressure, flow rates, etc. Additionally and/or alternatively, while the patterns are shown to be identical between each of the adjacent ducts 117, the pattern on the first duct may be different from the pattern on the second duct, if so desired.

Furthermore, any of the features in one embodiment may be combined with another feature from another embodiment depending upon the desired flow characteristics, e.g., pressure, flow rate, etc. For instance, the tapered height of the ducts 117 may be combined with openings 136 which are uniform in distribution or varied in distribution patterns and/or size of the openings. Other combinations are intended to be within the scope of the disclosure.

In addition to providing carbon dioxide to the plants on the rack system, embodiments of the present invention incorporate grow lights that emit light that is directed towards the plants. With reference to FIG. 8, a front view of an embodiment of the carbon dioxide distribution ducts 117 and grow light bar 145 used with the carbon dioxide distribution system 100 is illustrated. The grow light components can include a light ballast 143, a heat sink 141 and light bars 145 which hold a plurality of light emitting diodes (LEDs). Electrical power such as 110V AC or 220V AC is supplied to the light ballasts 143, which provide the required electrical power to the LED grow lights in the light bars 145. The ballasts 143 can limit the amount of current from supply line voltage, while maintaining the necessary electrical conditions for proper lamp start and operation. In this embodiment, the ballast 145 can be mounted under the lower surfaces of the air ducts 117. The ducts 117 can in physical contact with the light bars 145 and the ballasts 143. The ducts 117 can function as heat sinks for heat generated by the light bars 145 and the ballast 143. The ducts 117 can be dissipate the heat from the ballasts 143 and the light bars 145 to prevent over heating. Similarly, the heat sink 141 can help to dissipate the heat generated by the ballasts 143.

With reference to FIG. 9, a front view of another embodiment of the carbon dioxide distribution ducts 117 and grow lights 145 used with the carbon dioxide distribution system 100 is illustrated. In this embodiment, the light bar grow light bar 145 is supported by cables 149 which can be adjustable in length to adjust the height position of the light bar 145. The light bar 145 can be electrically coupled to the ballast 143 with an electrical cable 147.

In an embodiment with reference to FIG. 10, the filter housing 250 can include a pre-filter 251, disinfectant lights 255 and a secondary filter 253. The pre-filter 251 and the secondary filter 253 can be planar structures that are substantially parallel to each other. The lights 255 can be elongated tubular structures that extend across the width of the filter housing 250. In an embodiment, the lights 255 can be substantially parallel to each other and the pre-filter 251 and the secondary filter 253. The lights 255 can be vertically aligned with each other.

The Air exiting the filter housing 250 is directed towards the gas distribution ducts as described above. In the example, air is forced through a fan housing 103 and a pre-filter 251 into a light exposure space between the pre-filter 251 and a secondary filter 253. When the air is in between the pre-filter 251 and the secondary filter 253 the air is exposed to short-wavelength ultraviolet (UV-C) light, which results in ultraviolet germicidal irradiation (UVGI) of particles in the air. The UVGI is a disinfection method that uses UV-C light to kill or inactivate microorganisms by destroying nucleic acids. UVGI devices can produce strong enough UV-C light in circulating air systems to make them inhospitable environments to microorganisms such as bacteria, viruses, molds and other pathogens. UVGI can effectively provide air purification to the inlet air.

UV light is electromagnetic radiation with wavelengths shorter than visible light. UV can be separated into various ranges, with short-wavelength UV (UVC) considered "germicidal UV". At certain wavelengths, UV is mutagenic to bacteria, viruses and other microorganisms. Particularly at wavelengths around 250 nm-270 nm, UV breaks molecular bonds within microorganism DNA, producing thymine dimers that can kill or disable the organisms. In an embodiment, the system can have three 33 inch long, 120V, 25 Watt UV-C lamps that each produce a light intensity of 302 $\mu W/cm^2$. The lights are mounted in the plenum that eliminates surface bacteria, mold, and viruses from the system.

In different embodiments, various different types of lights can be used for the UVGI disinfectant air processing. For example, mercury-based lamps emit UV light at the 253.7 nm line, Ultraviolet Light Emitting Diodes (UV-C LED) lamps emit UV light at selectable wavelengths between 255 and 280 nm, and Pulsed-xenon lamps emit UV light across the entire UV spectrum with a peak emission near 230 nm.

The effectiveness of germicidal UV can depends on the length of time a microorganism is exposed to UV, the intensity and wavelength of the UV radiation, the presence of particles that can protect the microorganisms from UV, and a microorganism's ability to withstand UV during its exposure. In many systems, redundancy in exposing microorganisms to UV is achieved by circulating the air repeatedly. This ensures multiple passes so that the UV is effective against the highest number of microorganisms and will irradiate resistant microorganisms more than once to break them down.

The effectiveness of this form of disinfection depends on line-of-sight exposure of the microorganisms to the UV light. The lights 255 are placed in a direct line of sight for optimum for disinfection of the air. In an embodiment, the effectiveness and UV intensity can be achieved by using reflection. The interior surface of the filter housing 250 can have reflective surfaces so that the UV light can reflect back into the vent housing and expose more air to UV light. Aluminum can have a polished high reflectivity surface, which can improve the UVGI processing.

In air disinfection applications the UV effectiveness is estimated by calculating the UV dose which will be delivered to the microbial population. The UV dose is calculated through the equation: UV dose $\mu Ws/cm^2$=UV intensity $\mu W/cm^2 \times$ Exposure time (seconds). The UV intensity is specified for each lamp at a distance of 1 meter. In the air duct application, the exposure time is short so the UV intensity must be high and output by multiple UV lamps. The UV lights are located in a straight duct section with the lamps perpendicular to the air flow to maximize the exposure time. The UV dose is the amount of germicidal UV energy absorbed by a microbial population over a period of time. UVGI can be used to disinfect air with prolonged exposure. Disinfection is a function of UV intensity and time.

The pre-filters can keep dust particles out of the ducts of the system and prevent dust particles from being placed on the plants. The secondary filters can slow the air flow through the filter housing, giving the UV light more time to eliminate pathogens in the air. The pre-filter and the secondary filter are positioned to prevent light escaping the filter housing, which would be harmful to plants and people. The pre-filter and secondary filter can be carbon activated to reduce odors. The pre-filter and secondary filter can be black in color and absorb the light output by the UV light. The pre-filter and secondary filter can be opaque and the light output by the UV light from being transmitted through the pre-filter and secondary filter. The pre-filter and secondary filter does not reflect light which can prevent the UV light from escaping the filter housing.

Figure 11:
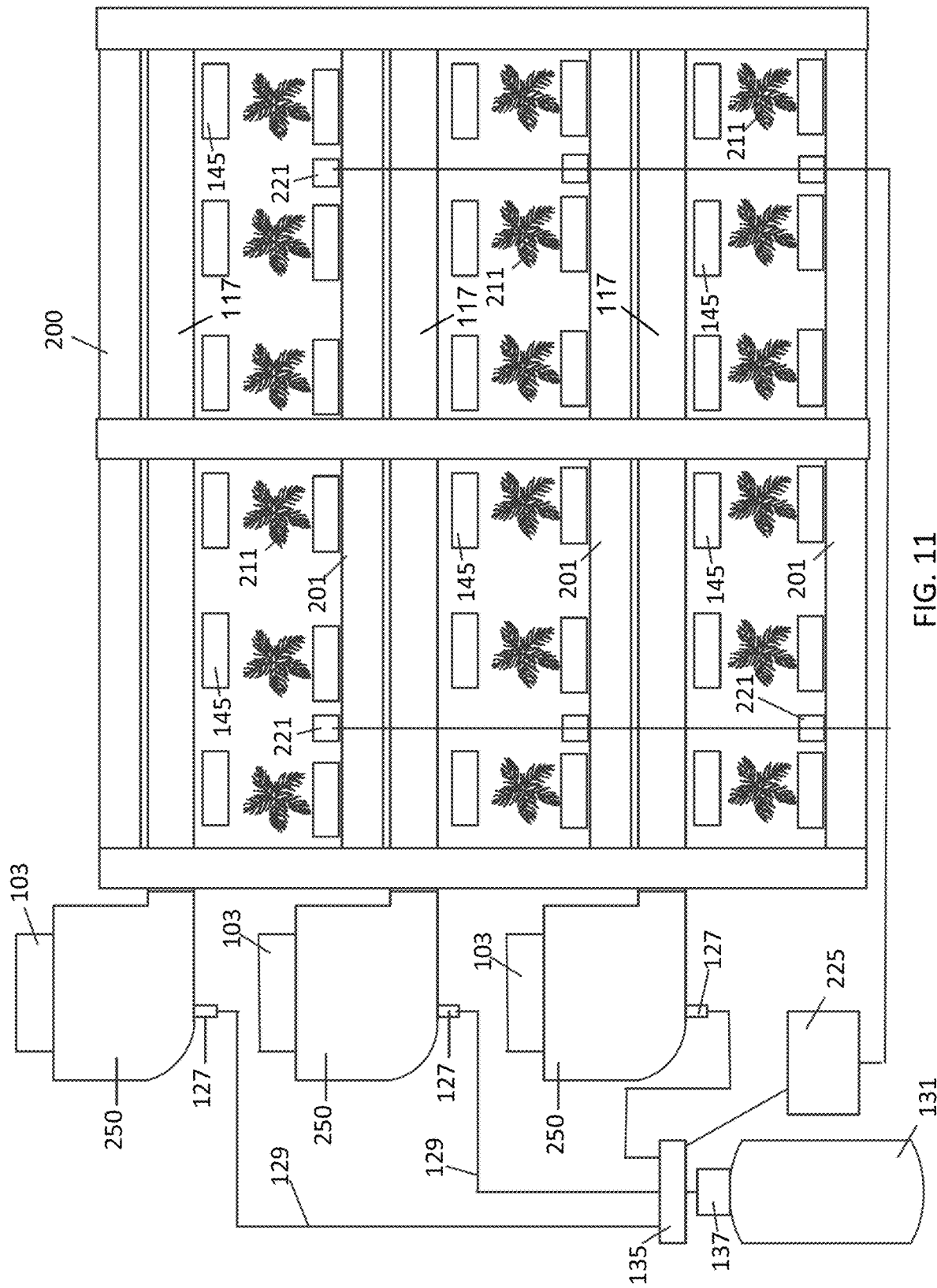
FIG. 11 illustrates a side view of multiple distribution systems installed on a rack system.

With reference to FIG. 11, the carbon dioxide distribution system can be used with a rack system 200 that includes a plurality of shelves 201 that provide a plurality of vertically aligned areas for growing plants 211. Air can be directed through fans 103 into filter housings 250 which can include a pre-filter, UV lights and a secondary filter. The pre-filter and secondary filter remove particles from the air and the UV light can disinfect the air. The purified air is mixed with the carbon dioxide and directed towards the ducts The ducts 117 of the carbon dioxide distribution systems can be mounted above each of the shelves 201 so that carbon dioxide can be delivered directly to the plants 211. The light bars 145 can also be mounted directly over the plants 211 so that exposure to the grow lights is maximized. An example of a pallet rack 200 is the PiPP mobile storage systems rack shelving system that has two basic components, beams and frames which are assembled to build racks with stacked shelves 201. http://www.pippmobile.com/Products/Shelving-Systems/Pallet-Rack.aspx The carbon dioxide system can be configured to maintain a specific level of carbon dioxide in a grow room. For example, in an embodiment, the system may be configured to maintain the carbon dioxide level at approximately 1,500 ppm. The system can include carbon dioxide sensors 221 coupled to a controller 225 that controls flow control values 135 coupled to the carbon dioxide source 131. By altering the positions of the control valves 135, the flow rates of carbon dioxide to the carbon dioxide distribution systems can be adjusted. The controller 225 can control the flow rate to maintain an optimum carbon dioxide level and prevent the carbon dioxide level from becoming dangerous. When the carbon dioxide level is too high (for example, above, 2,000 ppm), the sensors 221 can detect this excess carbon dioxide and reduce the flow rate of carbon dioxide into the distribution system. Conversely, if the carbon dioxide level is detected as being lower than 1,000 ppm, the controller 225 can open the control vales 135 to increase the carbon dioxide levels through the carbon dioxide distribution system. If the carbon dioxide source 131 is tanks a pressure sensor 137 can be mounted to the tank. If the pressure in the tank drops below a predetermined level, the system can inform the operator that the carbon dioxide tank should be replaced.

If the carbon dioxide level exceeds a level of 3,000, the system can issue a warning indicating that there can be a carbon dioxide control problem and the control system should be inspected. If the carbon dioxide level exceeds a level of 5,000, the system can issue a warning indicating that the carbon dioxide level exceeds the workplace exposure limit and warning people not to enter the room. With reference to Table 1 below a listing of carbon dioxide levels and the human reaction to exposure to the carbon dioxide gas.

TABLE 1

Listing of carbon dioxide levels and human reaction to exposure.

| Carbon Dioxide level | |
| --- | --- |
| 250-350 ppm | Normal carbon dioxide level in outdoor ambient air |
| 250-1,000 ppm | Normal carbon dioxide level in indoor air |
| 1,000-2,000 ppm | Poor quality air and complaints of drowsiness |
| 2,000-5,000 ppm | Headaches and sleepiness, increased heart rate and nausea. |
| 5,000+ ppm | Exceeds workplace exposure limit |

The ducts 117 can run along the length of the rack shelves 201 and the light bars 145 can extend across the width of the shelves 201. In this embodiment, the light bars 145 can be suspended with wires or other supports below the ducts. In other embodiments, the light bars 145 can be mounted directly to the bottom of the ducts 117. In an embodiment, the height of the light bars 145 over the plants 211 can be adjustable. The light bars 145 can be positioned so that the LED lights may be 12-18 inches above the plants 221. As the plants 211 grow, the vertical positions of the light bars 145 may be adjusted to provide the optimum grow light exposure to the plants 211.

While the openings distributed along the bottom of the ducts 117 may be varied in size, pattern, etc., additional features may be incorporated to further enhance the flow of air through the openings. One example is shown in the perspective view of FIG. 12A which illustrates flow diverters 260 which may be attached to or positioned into proximity of the openings, e.g., secured to the distal edge of the opening relative to the direction of airflow through the duct 117. The flow diverters 260 may be attached to one or more of the openings, e.g., to a select number of openings to enhance the flow along a particular region of the ducts, or to all the openings.

Figure 12B:
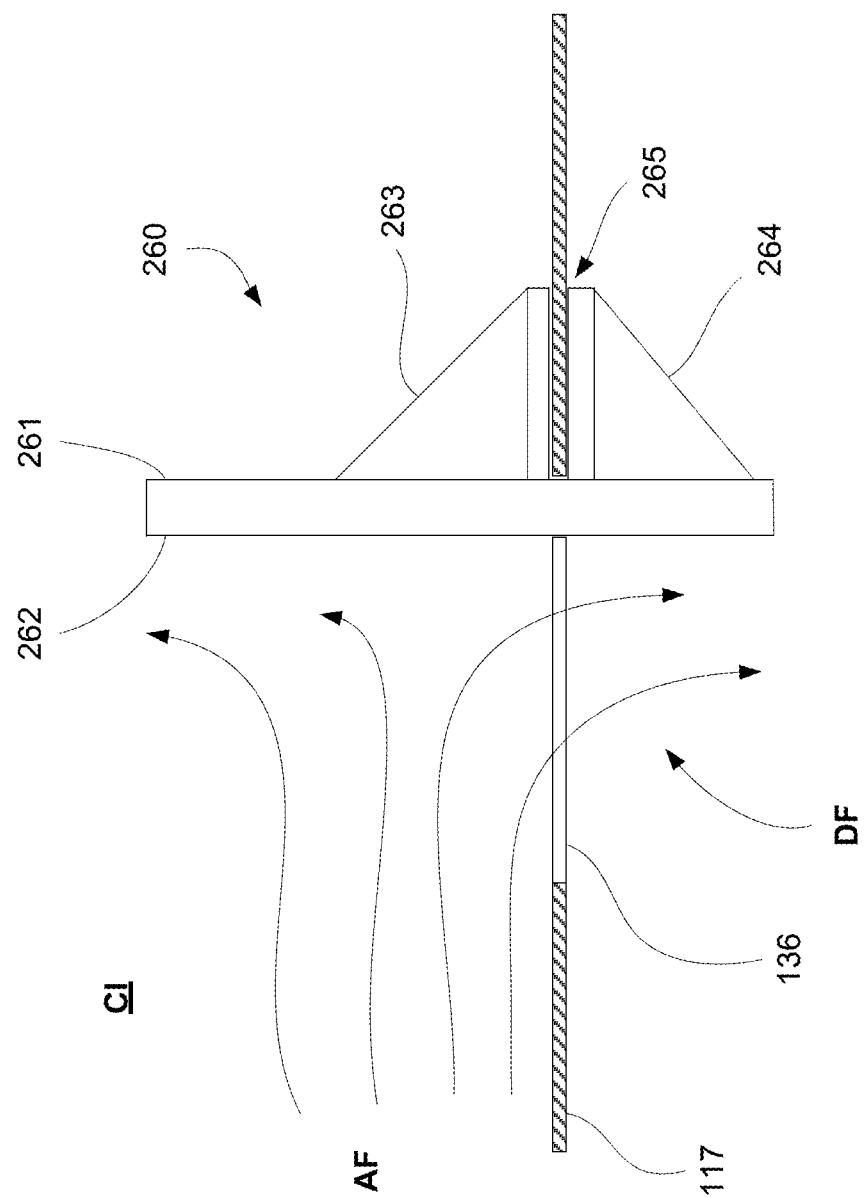
FIG. 12B illustrates a partial cross-sectional side view of a flow diverter attached to an opening.

One embodiment of a flow diverter 260 is shown in the partial cross-sectional side view of FIG. 12B which illustrates a flow diverter 260 attached to the opening 136. The flow diverter 260 may have a diverter platform 261 which defines a flow surface 262. The diverter platform 261 may incorporate a first gusset 263 and an apposed second gusset 264 such that the first gusset 263 and second gusset 264 extend towards one another to define a securement channel 265 which enables the flow diverter 260 to be removably slid upon a portion of the duct 117 and secured for use. As shown, a portion of the platform 261 may extend beyond the gussets 263, 264. As the flow diverter 260 may be configured for placement through the openings of the ducts 117, the diverter 260 may have a range of widths and a range of lengths. Moreover, while the diverter 260 is shown with a platform 261 which is flat, the platform 261 may be configured into other shapes, e.g., curved, convex, concave, etc.

Figures 13A, 13B:
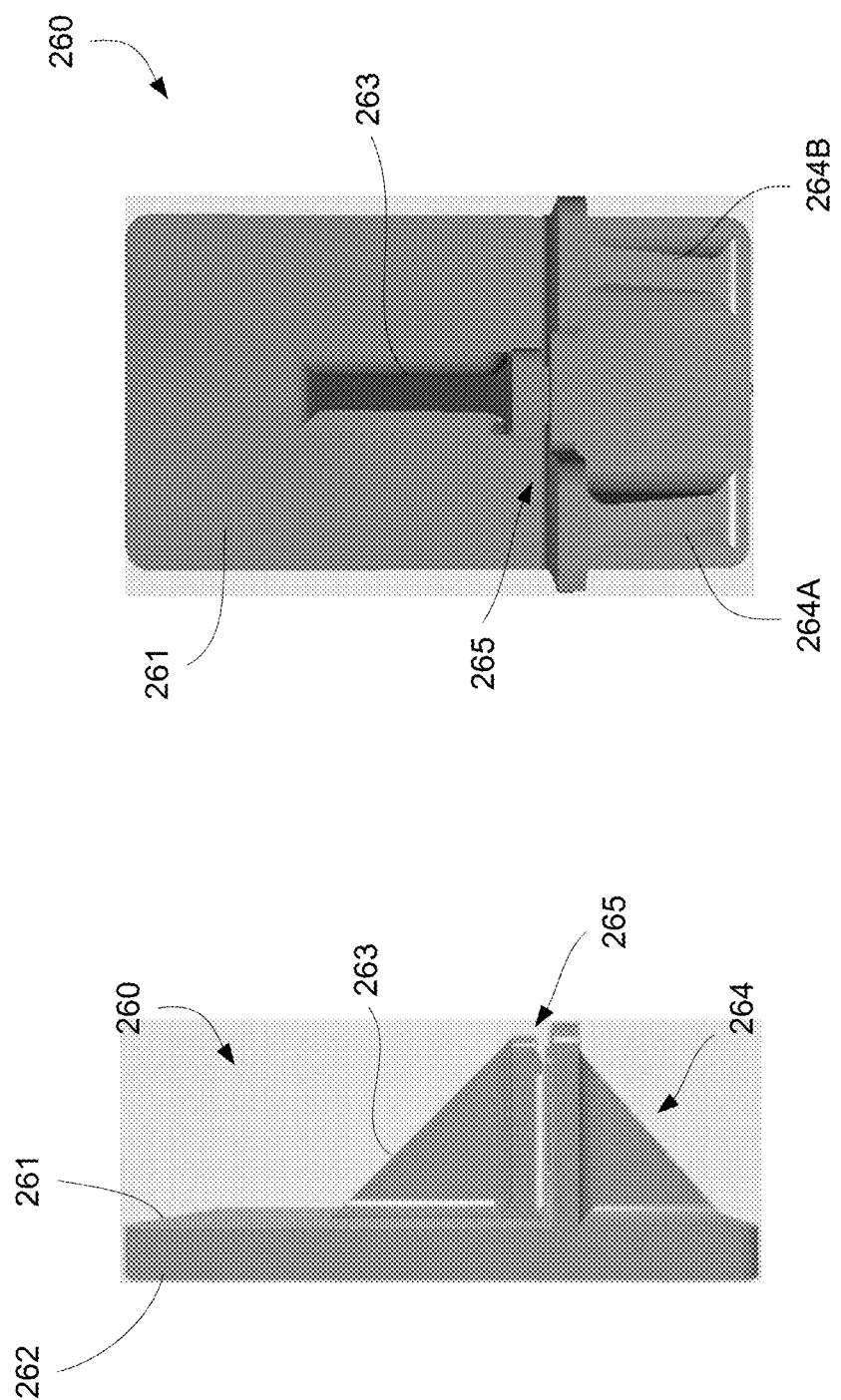
FIGS. 13A and 13B show side and rear views of an embodiment of the flow diverter.

In one example of use, the flow diverter 260 may be secured to the duct 117 so that the platform 261 extends at least partially into the channel interior CI so that a portion of the airflow AF encounters the flow surface 262 and is forced through the opening 136 as diverted flow DF. FIGS. 13A and 13B show side and rear views of an embodiment of the flow diverter 260. As illustrated, a single first gusset 263 may be positioned in apposition to two second gussets 264A, 264B so that the securement channel 265 for attachment to the duct 117 presents an alternating securement mechanism. Alternative securement mechanisms may also be incorporated with the flow diverter 260.

While the platform 261 may extend transversely, e.g., at 90°, into the channel interior CI relative to the duct 117 when the diverter 260 is secured for use, the platform 261 may be configured so that the platform 261 presents an angled flow surface 262 relative to the channel interior CI and duct surface. One embodiment is shown in the side view of FIG. 14A which illustrates a flow diverter 270 having an angled platform 261. The platform 261 is configured such that when secured for use, the flow surface 262 presents an acute angle $\Theta_1$, as illustrated by the angle $\Theta_1$ defined between the duct surface 271 and platform angle 272. The acute angle $\Theta_1$ may range from, e.g., 0° to 89°.

Figure 14B:
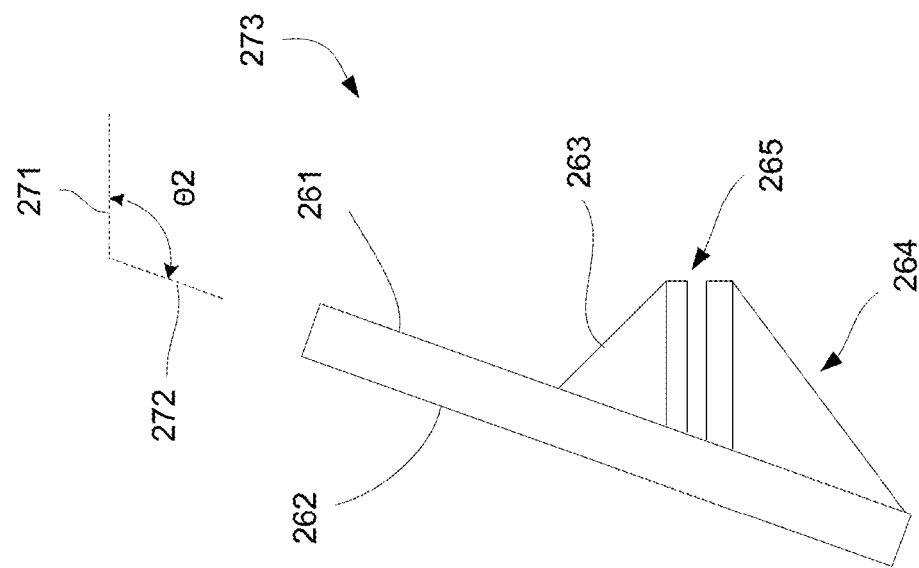
FIGS. 14A and 14B show side views of alternative embodiments of the flow diverter having angled platforms.
Figure 14A:
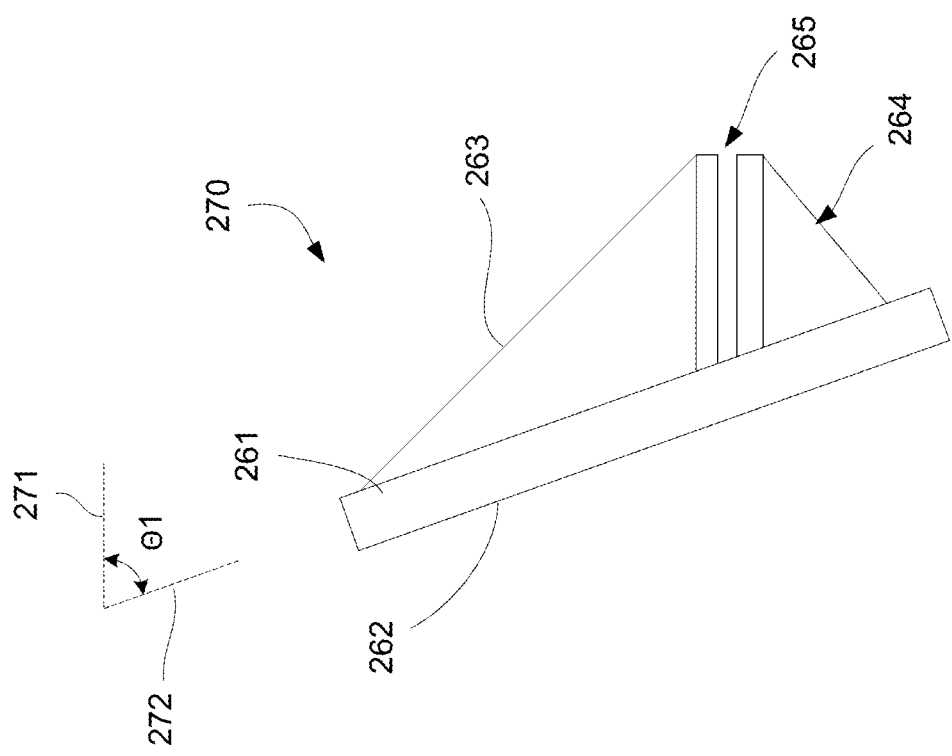

Another embodiment is shown in FIG. 14B which illustrates a flow diverter 273 having an angled platform 261 configured such that when secured for use, the flow surface 262 presents an obtuse angle $\Theta_2$ which may range from, e.g., 91° to 180°. The angle at which the platform 261 is configured may vary depending upon the desired amount of flow to be diverted through the opening.

It is intended that any of the flow diverters 260 may be used with any of the different distribution systems described herein and with any of the variations of the openings as well.

Figure 15A:
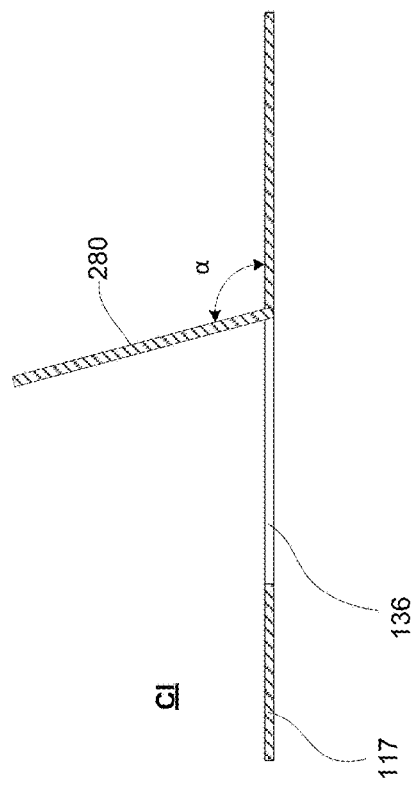
FIGS. 15A to 15C show cross-sectional side views of another embodiment in which the openings may be configured so that a portion of the duct wall may be pushed directly into the channel interior.
Figure 15B:
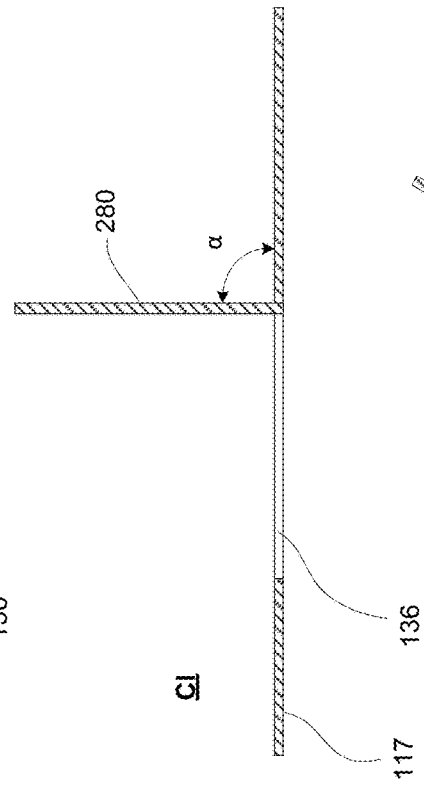
Figure 15C:
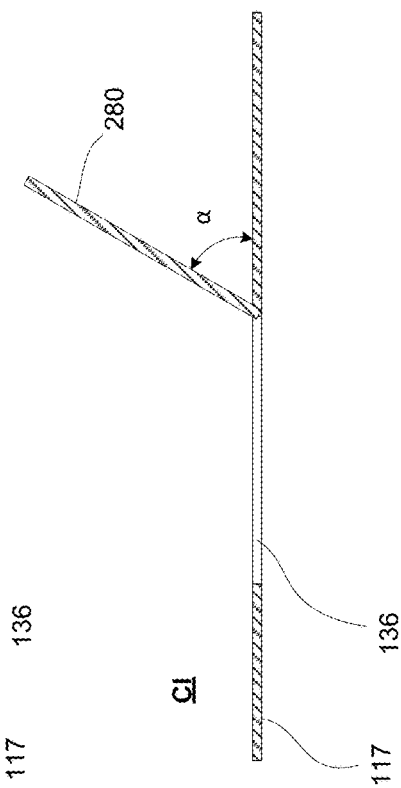

In another embodiment, the ducts may be configured to provide the flow diversion rather than attaching a separate mechanism. FIGS. 15A to 15C show cross-sectional side views of another variation in which the openings may be configured so that a portion of the duct wall may be pushed directly into the channel interior CI (e.g., push-in tab connected via a living hinge) to function as a flow diverter 280. As shown, the flow diverter 280 may be pushed into the channel interior CI so that the angle α defined by the diverter 280 relative to the duct surface forms an obtuse angle, as shown in FIG. 15A, a transverse right angle, as shown in FIG. 15B, or an acute angle, as shown in FIG. 15C.

In yet another variation, rather than utilizing racks which are separate from the ducts, the ducts 117 may be integrated directly with the racks to form a combined rack and air distribution system, as shown in the perspective view of FIG. 16. The rack system 300 may directly incorporate one or more of the ducts 117 directly below the shelves 301, 302 by being secured directly under the respective shelf, e.g., bolted, screwed, riveted, braced, etc. while the filter housing 101 and fan 105 may be mounted on one or both ends of each row or racking. With this embodiment and with any of the other embodiments described herein, the racks may incorporate a single shelf, two shelves, or multiple shelves (e.g., up to six shelves or more than six shelves) depending upon the desired number of shelves.

The braces supporting the rack 300 may also be configured to allow for the placement of the ducts 117 with minimal interference to the shelf platforms so that access to the shelves 301, 302 remains unhindered. In one embodiment, the braces may be configured into a diagonal cross-brace 304 between the rack supports while a second cross-brace 303 may extend horizontally between the rack supports relative to a surface of the shelf and positioned at a distance from the shelf surface so as to provide unhindered access to the shelf.

Figure 17:
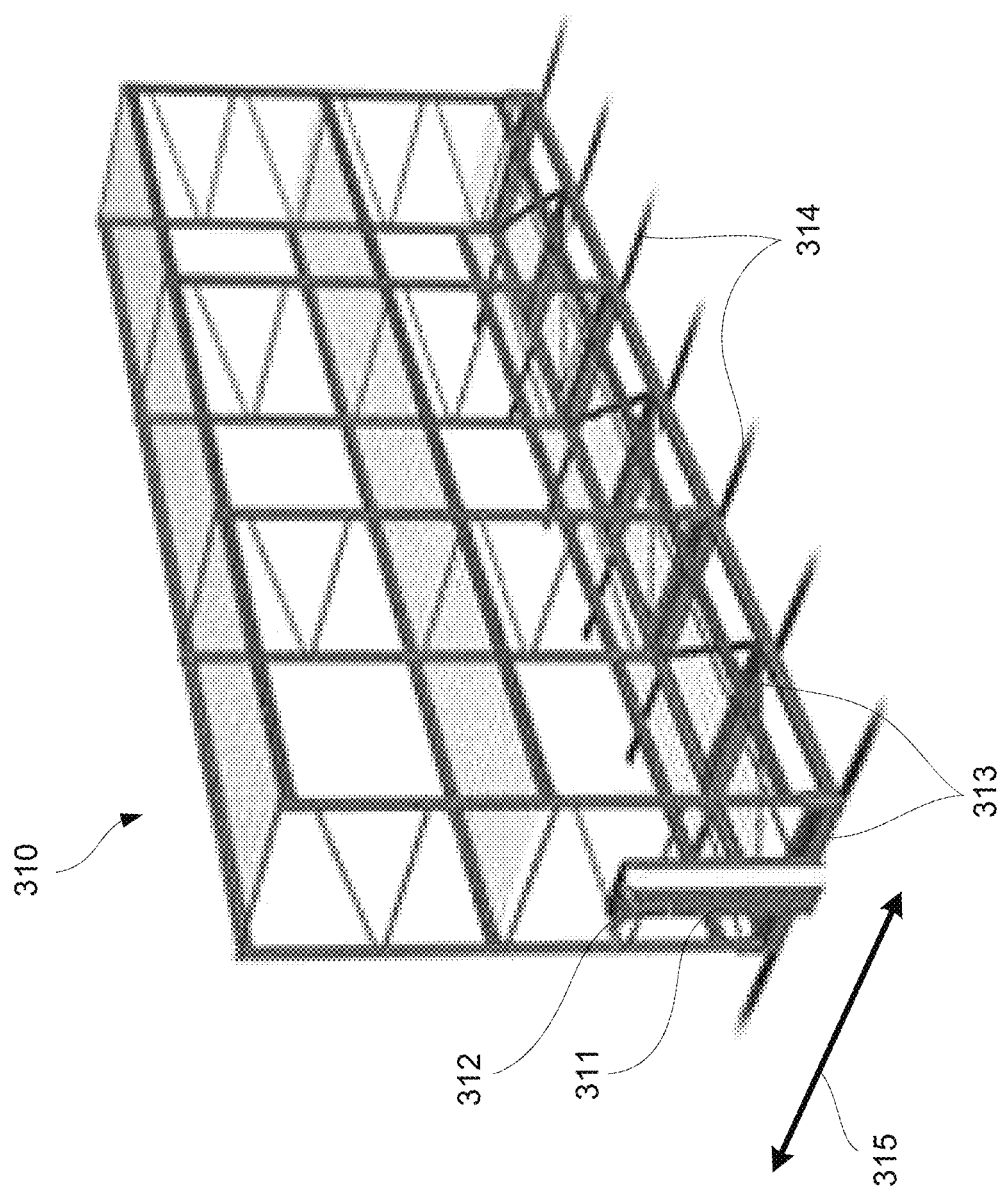
FIG. 17 shows a perspective view of another embodiment of a mobile rack configured to be re-positioned.

With this embodiment or any of the other rack and distribution systems described herein, any of the racks may be placed upon a floor or platform or secured in place upon the floor or platform. Alternatively, any of the racks may be configured to be mobile to allow for positioning or re-positioning of the racks relative to one another in order to facilitate access to multiple racks. An example of one embodiment is shown in the perspective view of FIG. 17 which illustrates a single mobile rack 310 having a controller unit 311 with an actuation mechanism 312 which may be used to move the rack 310. The rack 310 may be mounted upon one or more carriages 313 which can slide or roll upon one or more tracks 314 secured to the platform or floor. When the actuation mechanism 312 is actuated, e.g., mechanically, electronically, etc., the rack 310 may slide or roll upon the tracks 314 in a first or second direction 315.

Figure 18:
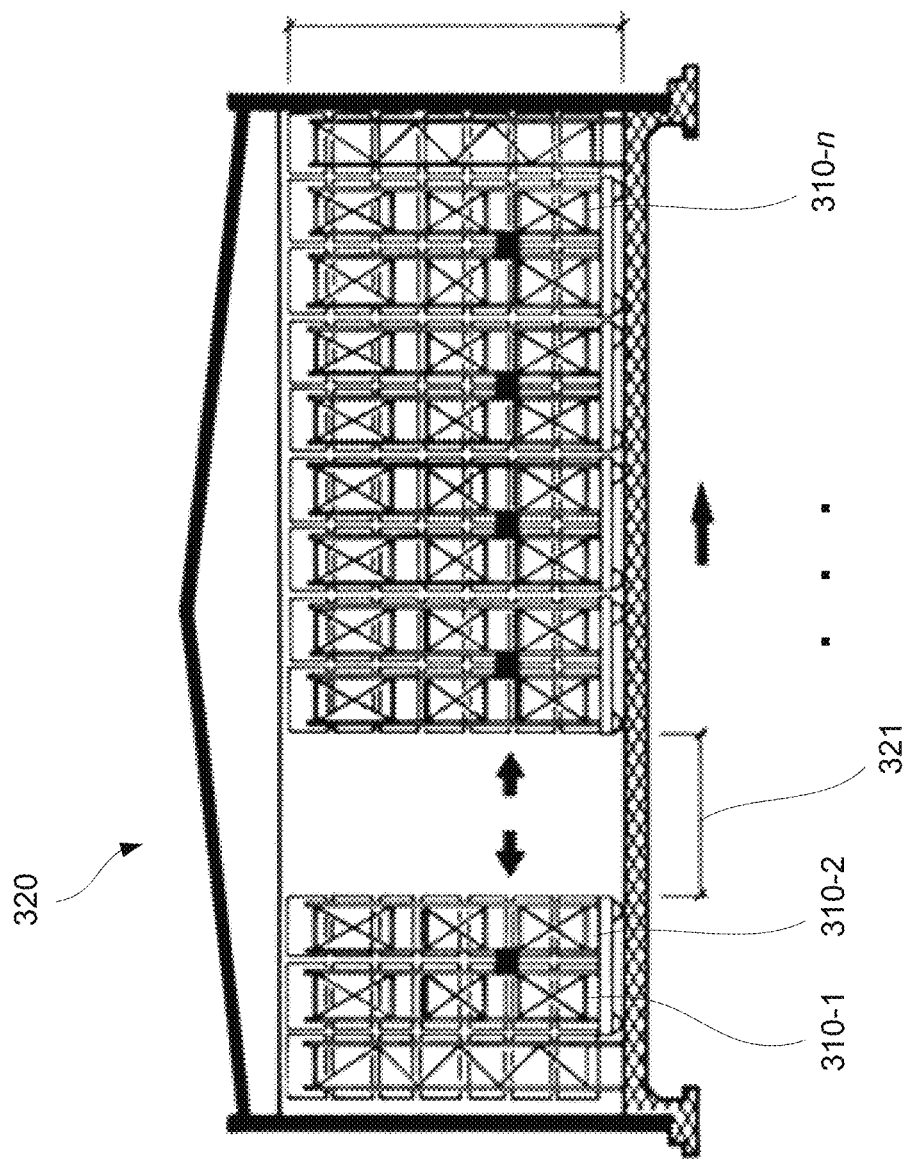
FIG. 18 shows an end view of a rack assembly showing multiple mobile racks which movable relative to one another.

FIG. 18 shows an end view of an example of a rack assembly 320 showing how multiple racks 310-1, 310-2, . . . , 310-*n* may be aligned directly adjacent to one another in order to preserve space for efficient vertical farming. The rows of racks may each have plants positioned upon their respective shelves and the distribution system positioned upon each rack may include any of the different embodiments described herein.

Each of the racks (or a select number of the racks) may be mounted upon a respective carriage 313 configured to slide or roll upon one or more tracks 314. Each of the racks may be positioned directly next to one another during use and when access to a particular rack is needed, the actuation mechanism 312 of a rack may be actuated to create a space 321 between the respective racks to provide sufficient access space. The racks may be moved individually or several at a time accordingly depending upon which rack is accessed.

The present disclosure, in various embodiments, includes components, methods, processes, systems and/or apparatus substantially as depicted and described herein, including various embodiments, subcombinations, and subsets thereof. Those of skill in the art will understand how to make and use the present disclosure after understanding the present disclosure. The present disclosure, in various embodiments, includes providing devices and processes in the absence of items not depicted and/or described herein or in various embodiments hereof, including in the absence of such items as may have been used in previous devices or processes, e.g., for improving performance, achieving ease and/or reducing cost of implementation. Rather, as the flowing claims reflect, inventive aspects lie in less than all features of any single foregoing disclosed embodiment.

What is claimed is:

1. A flow distribution assembly, comprising:
a housing having an air inlet portion;
a first elongated duct fluidly coupled to a first outlet portion of the housing and having a first plurality of openings defined on a lower surface of the first elongated duct;
a second elongated duct fluidly coupled to a second outlet portion of the housing adjacent to the first outlet portion and having a second plurality of openings defined on a lower surface of the second elongated duct, wherein the first elongated duct and second elongated duct extend adjacent to one another from the housing such that the first and second elongated ducts are configured to be positioned upon and extend through a rack, where the housing is directly secured to the first and second elongated ducts, and wherein air passing through the air inlet portion is received into the housing in a downward direction and the air passing through the first and second outlet portions is received into the first and second elongated ducts in a horizontal direction; and
one or more flow diverters which are removably positioned to slide upon a portion of the first elongated duct to project at least partially into the first elongated duct extending from at least one of the first plurality of openings.

2. The assembly of claim 1 further comprising:
a pre-filter;
a UV light; and
a secondary filter mounted in the housing distal to the air inlet portion.

3. The assembly of claim 2 further comprising a carbon dioxide input coupled to the housing, wherein the housing is configured to evenly distribute carbon dioxide with ambient air prior to distribution to the first and second elongated ducts.

4. The assembly of claim 3 further comprising a fan fluidly coupled to the housing, wherein the fan directs ambient air into the housing.

5. The assembly of claim 4 wherein filtered air is exposed to the UV light and mixed with the carbon dioxide, the air and carbon dioxide flows through the plurality of holes in the elongated duct to plants growing under the elongated duct.

6. The assembly of claim 4 wherein the fan directs the ambient air in a downward direction and the first elongated duct is oriented in a horizontal direction.

7. The assembly of claim 2 wherein the pre-filter and the secondary filter are each planar and substantially parallel and opaque to light emitted by the UV light.

8. The assembly of claim 2 wherein the UV light is positioned between the pre-filter and the secondary filter.

9. The assembly of claim 2 further comprising a second UV light mounted in the housing.

10. The assembly of claim 2 wherein the UV light outputs light wavelengths between 250 nm and 270 nm.

11. The assembly of claim 1 wherein at least the first plurality of openings comprise rectangular or square shapes.

12. The assembly of claim 1 wherein at least the first plurality of openings define an increasing size of the first plurality of openings distal to the filter housing.

13. The assembly of claim 1 wherein at least the first elongated duct tapers from a first height to a second height which is lower than the first height along a length of the first elongated duct.

14. The assembly of claim 1 wherein at least the first elongated duct defines a decreasing width of the first elongated duct along a length of the first elongated duct.

15. The assembly of claim 1 wherein the one or more flow diverters are configured for securement within or in proximity to at least one of the first plurality of openings.

16. The assembly of claim 15 wherein the one or more flow diverters comprises:
a diverter platform;
a first gusset; and
a second gusset apposed to the first gusset such that a securement channel is defined between first and second gussets.

17. The assembly of claim 16 wherein the diverter platform is angled relative to a surface of the first elongated duct.

18. The assembly of claim 1 wherein the first and second elongated ducts each have a height to width ratio of less than 0.25.

19. The assembly of claim 1 wherein the first and second elongated ducts each have a rectangular cross sectional area.

20. The assembly of claim 1 wherein the one or more flow diverters further extend externally through the at least one of the first plurality of openings.

21. The assembly of claim 1 further comprising at least one filter positioned in the housing proximal to the first and second outlet portions.

22. The assembly of claim 21 wherein the at least one filter is configured to receive spiraling air flow within the housing and to disrupt the air flow into an even distribution into the first and second outlet portions.

23. The assembly of claim 1 wherein the first elongated duct and second elongated duct define a space therebetween.

24. The assembly of claim 23 wherein the space between the first elongated duct and the second elongated duct is sized to accommodate at least one light ballast in a low profile configuration.

25. A flow distribution assembly, comprising:
a housing having an air inlet portion; and
an elongated duct fluidly coupled to an outlet portion of the housing and having a plurality of openings defined on a lower surface of the elongated duct, wherein the elongated duct extends from the housing and where the elongated duct is configured to be positioned upon and extend along a rack and where the housing is directly secured to the elongated duct, wherein air passing through the air inlet portion is received into the housing in a downward direction and the air passing through the outlet portion is received into the elongated duct in a horizontal direction.

26. The assembly of claim 25 further comprising a second elongated duct fluidly coupled to a second outlet portion of the housing adjacent to the outlet portion and having a second plurality of openings defined on a lower surface of the second elongated duct, wherein the second elongated duct extends adjacent to the elongate duct from the housing such that the flow distribution assembly with the elongated ducts is positionable upon a rack.

27. The assembly of claim 26 wherein the first elongated duct and second elongated duct define a space therebetween.

28. The assembly of claim 27 wherein the space between the elongated duct and the second elongated duct is sized to accommodate at least one light ballast in a low profile configuration.

29. The assembly of claim 25 further comprising:
a pre-filter;
a UV light; and
a secondary filter mounted in the housing distal to the air inlet portion.

30. The assembly of claim 29 further comprising a carbon dioxide input coupled to the housing, wherein the housing is configured to evenly distribute carbon dioxide with ambient air prior to distribution to the elongated duct.

31. The assembly of claim 30 further comprising a fan fluidly coupled to the housing, wherein the fan directs ambient air into the housing.

32. The assembly of claim 31 wherein air is exposed to the UV light and mixed with the carbon dioxide, the air and carbon dioxide flows through the plurality of holes in the elongated duct to plants growing under the elongated duct.

33. The assembly of claim 31 wherein the fan directs the ambient air in a downward direction and the elongated duct is oriented in a horizontal direction.

34. The assembly of claim 29 wherein the pre-filter and the secondary filter are each planar and substantially parallel and opaque to light emitted by the UV light.

35. The assembly of claim 29 wherein the UV light is positioned between the pre-filter and the secondary filter.

36. The assembly of claim 29 further comprising a second UV light mounted in the housing.

37. The assembly of claim 29 wherein the UV light outputs light wavelengths between 250 nm and 270 nm.

38. The assembly of claim 25 wherein at least the first plurality of openings comprise rectangular or square shapes.

39. The assembly of claim 25 further comprising at least one filter positioned in the housing proximal to the outlet portion.

40. The assembly of claim 39 wherein the at least one filter is configured to receive spiraling air flow within the housing and to disrupt the air flow into an even distribution into the outlet portions.

41. The assembly of claim 25 further comprising one or more flow diverters which are removably positioned to slide upon a portion of the elongated duct to project at least partially into the elongated duct extending from at least one of the plurality of openings.

42. The assembly of claim 41 wherein the one or more flow diverters are configured for securement within or in proximity to at least one of the plurality of openings.

43. The assembly of claim 42 wherein the one or more flow diverters comprises:
a diverter platform;
a first gusset; and
a second gusset apposed to the first gusset such that a securement channel is defined between first and second gussets.

44. The assembly of claim 41 wherein the one or more flow diverters further extend externally through the at least one of the plurality of openings.

45. A flow distribution system, comprising:
a rack having at least a first platform and a second platform positioned below the first platform;
a housing having an air inlet portion;
an elongated duct fluidly coupled to an outlet portion of the housing and having a plurality of openings defined on a lower surface of the elongated duct, wherein the elongated duct extends from the housing and where the elongated duct is configured to be positioned below the first platform and extend through the rack such that the plurality of openings are directed towards the second platform underlying the first platform, wherein air passing through the air inlet portion is received into the housing in a downward direction and the air passing through the outlet portion is received into the elongated duct in a horizontal direction; and
a fan fluidly coupled to the housing and extending away from the rack and where the housing is directly secured to the elongated duct.

46. The system of claim 45 further comprising one or more flow diverters which are removably positioned to slide upon a portion of the elongated duct to project at least partially into the elongated duct extending from at least one of the plurality of openings.

47. The system of claim 46 wherein the one or more flow diverters are configured for securement within or in proximity to at least one of the plurality of openings.

48. The system of claim 46 wherein the one or more flow diverters comprises:
a diverter platform;
a first gusset; and
a second gusset apposed to the first gusset such that a securement channel is defined between first and second gussets.

49. The system of claim 46 wherein the one or more flow diverters further extend externally through the at least one of the plurality of openings.

50. The system of claim 45 further comprising a second elongated duct fluidly coupled to a second outlet portion of the housing adjacent to the outlet portion and having a second plurality of openings defined on a lower surface of the second elongated duct, wherein the second elongated duct extends adjacent to the elongate duct from the housing such that the flow distribution assembly with the elongated ducts is positionable upon the rack.

51. The system of claim 45 further comprising:
a pre-filter;
a UV light; and
a secondary filter mounted in the filter housing distal to the air inlet portion.

52. The system of claim 51 further comprising a carbon dioxide input coupled to the housing, wherein the housing is configured to evenly distribute carbon dioxide with ambient air prior to distribution to the first and second elongated ducts.

53. The system of claim 52 wherein filtered air is exposed to the UV light and mixed with the carbon dioxide, the air and carbon dioxide flows through the plurality of holes in the elongated duct to plants growing under the elongated duct.

54. The system of claim 51 wherein the pre-filter and the secondary filter are each planar and substantially parallel and opaque to light emitted by the UV light.

55. The system of claim 51 wherein the UV light is positioned between the pre-filter and the secondary filter.

56. The system of claim 51 further comprising a second UV light mounted in the housing.

57. The system of claim 51 wherein the UV light outputs light wavelengths between 250 nm and 270 nm.

58. The system of claim 45 wherein the fan directs ambient air into the housing.

59. The system of claim 45 wherein the fan directs the ambient air in a downward direction and the elongated duct is oriented in a horizontal direction.

60. The system of claim 45 wherein the plurality of openings comprise rectangular or square shapes.

* * * * *

(12) INTER PARTES REVIEW CERTIFICATE (3397th)

United States Patent
Bogner et al.

(10) Number: US 10,806,099 K1
(45) Certificate Issued: Jan. 29, 2024

(54) SYSTEM AND METHOD FOR PROVIDING CARBON DIOXIDE AND CIRCULATING AIR FOR A VERTICAL GARDENING SYSTEM

(71) Applicants: Matthew Lawrence Bogner; James Allen Cunningham

(72) Inventors: Matthew Lawrence Bogner; James Allen Cunningham

(73) Assignee: PIPP MOBILE STORAGE SYSTEMS, INC.

Trial Number:

IPR2022-00893 filed Apr. 19, 2022

Inter Partes Review Certificate for:

Patent No.: 10,806,099
Issued: Oct. 20, 2020
Appl. No.: 16/112,077
Filed: Aug. 24, 2018

The results of IPR2022-00893 are reflected in this inter partes review certificate under 35 U.S.C. 318(b).

INTER PARTES REVIEW CERTIFICATE
U.S. Patent 10,806,099 K1
Trial No. IPR2022-00893
Certificate Issued Jan. 29, 2024

AS A RESULT OF THE INTER PARTES REVIEW PROCEEDING, IT HAS BEEN DETERMINED THAT:

Claims 25-27, 45, 50, 58 and 59 are cancelled.

\* \* \* \* \*